US012703882B2

(12) United States Patent
Vollmers et al.

(10) Patent No.: US 12,703,882 B2
(45) Date of Patent: Aug. 11, 2026

(54) METHODS OF SEQUENCING ANTIBODY CHAINS FROM HYBRIDOMAS AND KITS FOR PRACTICING SAME

(71) Applicant: The Regents of the University of California, Oakland, CA (US)

(72) Inventors: Christopher Vollmers, Santa Cruz, CA (US); Rebecca DuBois, Santa Cruz, CA (US); Lena Ricemeyer, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 428 days.

(21) Appl. No.: 16/900,541

(22) Filed: Jun. 12, 2020

(65) Prior Publication Data

US 2020/0392578 A1 Dec. 17, 2020

Related U.S. Application Data

(60) Provisional application No. 62/861,844, filed on Jun. 14, 2019.

(51) Int. Cl.

| | |
|---|---|
| ***C12Q 1/6876*** | (2018.01) |
| ***C12N 15/10*** | (2006.01) |
| ***C12Q 1/6869*** | (2018.01) |

(52) U.S. Cl.

CPC ....... *C12Q 1/6876* (2013.01); *C12N 15/1096* (2013.01); *C12Q 1/6869* (2013.01); *C12Q 2525/155* (2013.01); *C12Q 2535/101* (2013.01)

(58) Field of Classification Search

CPC ................ C12Q 1/6876; C12Q 1/6869; C12Q 2525/155; C12Q 2535/101; C12N 15/1096

See application file for complete search history.

(56) References Cited

U.S. PATENT DOCUMENTS 5,962,271 A 10/1999 Chenchik et al.
5,962,272 A 10/1999 Chenchik et al.

(Continued)

OTHER PUBLICATIONS

Meyer et al. A simplified workflow for monoclonal antibody sequencing. PLoS One 2019; 14(6): e0218717. (Year: 2019).*

(Continued)

*Primary Examiner* — Aaron A Priest
*Assistant Examiner* — Tian Yu
(74) *Attorney, Agent, or Firm* — Brian E. Davy; Bozicevic, Field & Francis LLP

(57) ABSTRACT

Aspects of the present disclosure include methods of sequencing antibody chains from hybridomas. In some embodiments, the methods comprise contacting hybridoma RNA with a constant region-specific reverse transcription primer, and contacting the hybridoma RNA with a reverse transcriptase with terminal nucleotidyl transferase activity, thereby creating a heavy chain and/or light chain cDNA. Such methods further comprise contacting the cDNA with a template switch oligonucleotide comprising a universal PCR primer sequence, thereby generating a single stranded cDNA, and performing second strand synthesis on the single stranded cDNA, thereby producing a double stranded heavy chain and/or light chain cDNA. A heavy chain and/or light chain sequencing template is produced, and the methods further comprise sequencing the template by Sanger sequencing. Also provided are kits that find use, e.g., in practicing the methods of the present disclosure.

4 Claims, 8 Drawing Sheets

Specification includes a Sequence Listing.

(56) References Cited

U.S. PATENT DOCUMENTS

2013/0018173 A1* 1/2013 Simard .................. C07K 16/24 506/17
2013/0023009 A1* 1/2013 Kurosawa .......... C12N 15/1027 435/69.6
2014/0357500 A1* 12/2014 Vigneault .......... C12N 15/1093 506/4
2016/0252495 A1* 9/2016 Ricicova .............. G01N 33/505 506/9
2016/0265050 A1* 9/2016 Sahin ................... C12Q 1/6881

OTHER PUBLICATIONS

Chen et al. Reverse transcriptase adds nontemplated nucleotides to cDNAs during 5'-RACE and primer extension. BioTechniques 2001; 30: 574-582 (Year: 2001).*
10x Genomics | CG000108 Rev A Technical Note—Assay Scheme and Configuration of Chromium™ Single Cell 3' v2 Librarie (Year: 2017).*
Simple Cloning Lab: Hybridisation ; www.bioinformatics.nl; Archived Aug. 10, 2017 on WaybackMachine (Year: 2017).*
Kit SMARTer® RACE 5'/3'; Published by Clontech in 2015 (Year: 2015).*
Zhu et al. Reverse transcriptase template switching: a SMART approach for full-length cDNA library construction. Biotechniques. Apr. 2001;30(4):892-7. doi: 10.2144/01304pf02. PMID: 11314272 (Year: 2001).*
Harding et al. The immunogenicity of humanized and fully human antibodies: residual immunogenicity resides in the CDR regions. MAbs. May-Jun. 2010;2(3):256-65. doi: 10.4161/mabs.2.3.11641. Epub May 1, 2010. PMID: 20400861; PMCID: PMC2881252. (Year: 2010).*
Clontech (Kit SMARTer® RACE 5'/3'; Published by Clontech in 2015); previously cited (Year: 2015).*
Larrick, et al. Polymerase chain reaction using mixed primers: cloning of human monoclonal antibody variable region genes from single hybridoma cells Bio/Technology 7:934 (1989)) (Year: 1989).*
5' RACE System for Rapid Amplification of cDNA Ends _ Thermo Fisher Scientific ; Archived on Wayback Machine Oct. 24, 2015 (Year: 2015).*
Babrak et al. (2017) "Identification and verification of hybridoma-derived monoclonal antibody variable region sequences using recombinant DNA technology and mass spectrometry" Mol Immunol, 90:287-294.
Bandeira et al. (2008) Beyond Edman Degradation: Automated de novo protein sequencing of monoclonal antibodies. Nat Biotechnol, 26(12):1336-1338.
Barouch et al. (2005) "A human T-cell leukemia virus type 1 regulatory element enhances the immunogenicity of human immunodeficiency virus type 1 DNA vaccines in mice and nonhuman primates" J Virol, 79(14):8828-8834.
Bogdanoff et al. (2016) "De Novo Sequencing and Resurrection of a Human Astrovirus-Neutralizing Antibody" ACS Infect Dis. 2:313-321.
Castellana et al. (2011) "Resurrection of a clinical antibody: template proteogenomic de novo proteomic sequencing and reverse engineering of an anti-lymphotoxin-alpha antibody" Proteomics, 11(3):395-405.
Coco-Martin et al. (1991) "Methods for studying the stability of antibody expression by hybridoma cells in homogeneous continuous culture systems" Analytica Chimica Acta, 249(1):257-262.
Doenecke et al. (1997) "Rapid amplification of cDNA ends (RACE) improves the PCR-based isolation of immunoglobulin variable region genes from murine and human lymphoma cells and cell lines" Leukemia, 11:1787-1792.
Espinosa et al. (2019) "Isolation of neutralizing monoclonal antibodies to human astrovirus and characterization of virus variants that escape neutralization" J Virol, 93(2):e01465-18.
Frenzel et al.(2013) "Expression of recombinant antibodies" Front Immunol, 4(217):1-20.
Henry et al. (2018) "Next-Generation DNA Sequencing of VH/VL Repertoires: A Primer and Guide to Applications in Single-Domain Antibody Discovery" Methods Mol Biol, 425-446.
Ihle et al. (2003) "Cloning, sequencing and expression of immunoglobulin variable regions of murine monoclonal antibodies specific for the P1.7 and P1.16 PorA protein loops of Neisseria meningitidis" Scand J Immunol, 57:453-462.
Koren et al. (2008) "Antibody variable-region sequencing as a method for hybridoma cell-line authentication" Appl Microbiol Biotechnol, 78:1071-1078.
Krebber et al. (1997) "Reliable cloning of functional antibody variable domains from hybridomas and spleen cell repertoires employing a reengineered phage display system" J Immunol Methods, 201:35-55.
Kuniyoshi et al. (2016) "Identification of Immunoglobulin Gene Sequences from a Small Read No. of mRNA-Seq Using Hybridomas" PLoS One, 11:e0165473.
Lefranc et al. (2004) "IMGT, The International ImMunoGeneTics Information System" Methods Mol Biol, 248:27-49.
Rickert et al. (2016) "Combining phage display with de novo protein sequencing for reverse engineering of monoclonal antibodies" MABS, 8(3):501-512.
Ruberti et al. (1994) "The use of the RACE method to clone hybridoma cDNA when V region primers fail" J Immunol Methods. 173(1):33-39.
Schanz et al. (2014) "High-throughput sequencing of human immunoglobulin variable regions with subtype identification" PLoS One, 9(11):e111726.
Sen et al. (2017) "Automated Antibody De Novo Sequencing and Its Utility in Biopharmaceutical Discovery" J Am Soc Mass Spectrom, 28:803-810.
Sievers et al. (2011) "Fast, scalable generation of high-quality protein multiple sequence alignments using Clustal Omega" Mol Syst Biol, 7:539.
Smith et al. (1986) "Fluorescence detection in automated DNA sequence analysis" Nature, 321:674-679.
Walker et al. (2008) "RNA Affinity Tags for the Rapid Purification and Investigation of RNAs and RNA-Protein Complexes" Methods Mol Biol., 488:23-40.
Wang et al. (2000) "Universal PCR amplification of mouse immunoglobulin gene variable regions: the design of degenerate primers and an assessment of the effect of DNA polymerase 3' to 5' exonuclease activity" J Immunol Methods, 233(1-2):167-177.
Waterhouse et al. (2009) Jalview Version 2—a multiple sequence alignment editor and analysis workbench. Bioinformatics, 25(9):1189-1191.
Wilson & Szostak (1999) "In Vitro Selection of Functional Nucleic Acids" Annu Rev Biochem., 68:611-647.
Wu et al. (2015) "Maturation and Diversity of the VRC01-Antibody Lineage over 15 Years of Chronic HIV-1 Infection" Cell, 161:470-485.
Ye et al. (2013) "IgBLAST: an immunoglobulin variable domain sequence analysis tool" Nucleic Acids Res, 41:W34-W40.
Zhou et al. (2010) "Structural basis for broad and potent neutralization of HIV-1 by antibody VRC01" Science, 329(5993):811-817.
Zhu et al. (2001) "Reverse transcriptase template switching: a SMART approach for full-length cDNA library Construction" Biotechniques, 30(4):892-897.
Takara "Rapid cloning of antibody variable regions using SMART technology" Takarabio.com, 5 pp.

* cited by examiner

Step 1: Reverse transcription begins.

Step 2: Reverse transcriptase adds CCC.

Step 3: Template-switch oligo binds CCC.

Step 4: Template switching occurs.

A
kb
3
1
0.5
kb ladder
2D9
K L H
3B4
K L H
3E8
K L H
kb ladders
3H4
K L H
4B6
K L H
kb ladder
B
kb
3
1
0.5
kb ladder
2D9
K L H
3B4
K L H
3E8
K L H
kb ladders
3H4
K L H
4B6
K L H
kb ladder B
Spike 8/Chimeric mAb 2D9
Spike 8/No 1° Ab
BSA/Chimeric mAb 2D9
Absorbance at 490 nm
0
0.5
1
1.5
2
2.5
3
3.5
[Chimeric mAb 2D9] in ng/mL
0.01
0.1
1
10
100
1000
10000

METHODS OF SEQUENCING ANTIBODY CHAINS FROM HYBRIDOMAS AND KITS FOR PRACTICING SAME

CROSS-REFERENCE TO RELATED APPLICATIONS

This application claims the benefit of U.S. Provisional Patent Application No. 62/861,844, filed Jun. 14, 2019, which application is incorporated herein by reference in its entirety.

STATEMENT OF GOVERNMENT SUPPORT

This invention was made with Government support under Grant No. AI130073, awarded by the National Institutes of Health. The Government has certain rights in the invention.

INCORPORATION BY REFERENCE OF SEQUENCE LISTING PROVIDED AS A TEXT FILE

A Sequence Listing is provided herewith in a text file, UCSC-387_Seq_List_ST25, created on Jul. 28, 2023 and having a size of 4,306 bytes. The contents of the text file are incorporated herein by reference in its entirety.

INTRODUCTION

Recombinant monoclonal antibodies (mAbs) are a multibillion-dollar industry. In contrast to monoclonal antibodies generated using traditional hybridoma-based methods and isolated from ascites fluid, recombinant monoclonal antibodies are produced by cloning antibody cDNA or synthetic sequences into expression plasmids and expressing in mammalian cell culture. (Reference 1). Before the design of recombinant antibody expression plasmids, sequencing of the antibody light and heavy chain variable regions is required. These variable regions determine antigen binding. It is therefore critical to obtain the correct sequence of the variable regions to maintain antibody affinity and specificity. In addition, knowledge of the variable region sequences and subsequent recombinant antibody expression reduces the impact of hybridoma cell loss and hybridoma instability caused by mutations, chromosome deletions, or environmental factors. (Reference 2)

There are several existing methods to sequence antibody variable regions from hybridoma cells or lymphocytes. Some involve the use of high-throughput RNA-sequencing technologies. (References 3-5) However, most labs are not familiar with or do not have access to high-throughput sequencing technologies, which require expertise for the preparation of RNA-seq libraries and for computational analysis. Furthermore, the cost of high-throughput library preparation and sequencing can be substantial, and the tur around time at high throughput sequencing cores can be weeks to months.

Other methods to sequence antibody variable regions use PCR and Sanger sequencing. Variable region sequence determination by PCR-based approaches is challenging due to difficulties in designing universal primers that amplify all possible variable region sequences. This problem arises as a result of the inherent low sequence identity in the 5' leader sequence of antibody light and heavy chains, directly upstream of the variable regions. Some approaches use sets of degenerate primers targeting the 5' region to overcome this issue. (References 6-9) However, these degenerate primers sometimes result in amplification success rates of only 80-90% because of non-specific priming or no priming. (References 6,9) An additional risk with degenerate primers is that the variable regions of the parent myeloma cell line can also amplify using these primers. (Reference 9) Other approaches use 5' RACE (rapid amplification of 5' cDNA ends), (References 10,11) but mRNA degradation, cDNA purification, and polyA tail addition in between reverse transcription and PCR makes this approach less efficient. (Reference 12) A technique using non-degenerate primers also exists, but with this technique, each variable region needs multiple amplification attempts with different sets of primers as well as further sequence validation with mass spectrometry. (Reference 13). Furthermore, there is a non-negligible risk of introducing primer-derived mutations using these methods.

In addition to nucleic acid-based approaches, there are de novo protein sequencing approaches to determine antibody variable regions by mass spectrometry (References 14-16), but these methods do not always lead to a single variable region sequence due to isobaric residues such as isoleucine and leucine (Reference 17). A combination of X-ray crystallography and mass spectrometry positively identified variable region sequences (Reference 18). However, this method is time-consuming, requires large amounts of purified monoclonal antibody, and is expensive.

Finally, researchers without access to these technologies may employ antibody sequencing services, such as those provided by GenScript, Syd Labs, Fusion Antibodies, or LakePharma. (References 19-22). Unfortunately, these services can become prohibitively expensive, costing at least $800 to sequence a single antibody's variable regions. Inexpensive but accurate and effective methods of antibody sequencing are clearly required.

SUMMARY

Aspects of the present disclosure include methods of sequencing antibody chains from hybridomas. In some embodiments, the methods comprise contacting hybridoma RNA with a constant region-specific reverse transcription primer, and contacting the hybridoma RNA with a reverse transcriptase with terminal nucleotidyl transferase activity, thereby creating a heavy chain and/or light chain cDNA. Such methods further comprise contacting the heavy chain and/or light chain cDNA with a template switch oligonucleotide comprising a universal PCR primer sequence, thereby generating a heavy chain and/or light chain single stranded cDNA, and performing second strand synthesis on the heavy chain and/or light chain single stranded cDNA, thereby producing a double stranded heavy chain and/or light chain cDNA. Such methods further comprise contacting the double stranded heavy chain and/or light chain cDNA with a universal PCR primer that hybridizes to the template switch oligonucleotide and a constant region specific PCR primer, where the constant region specific PCR primer binds to a different sequence than the constant region specific reverse transcription primer, thereby producing a heavy chain and/or light chain sequencing template. Sanger sequencing is performed on the heavy chain and/or light chain sequencing template. Also provided are kits that find use, e.g., in practicing the methods of the present disclosure.

DETAILED DESCRIPTION

Figure 1:
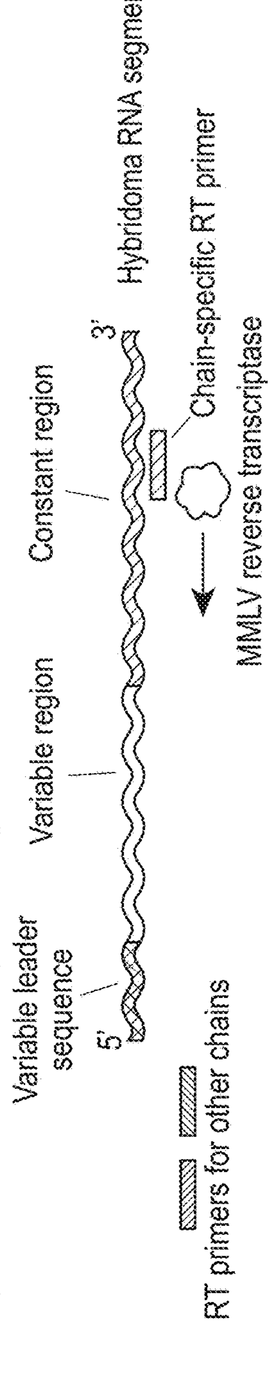
FIG. 1: An illustration of the disclosed method according to some embodiments.
Figure 1:
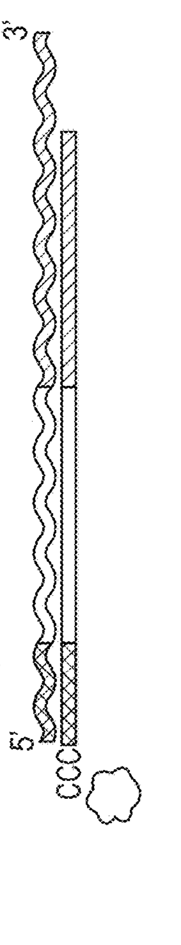
Figure 1:
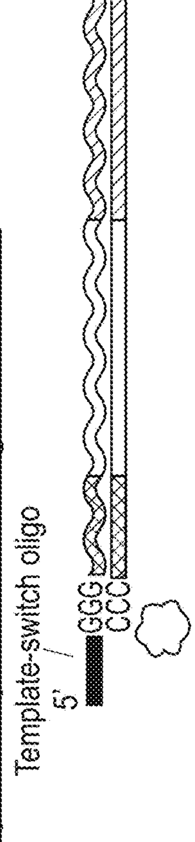
Figure 1:
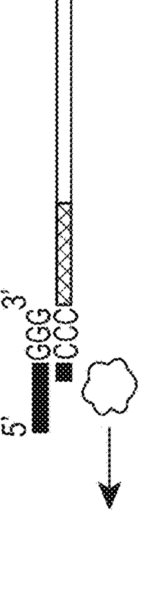
Figure 1:
Figure 1:
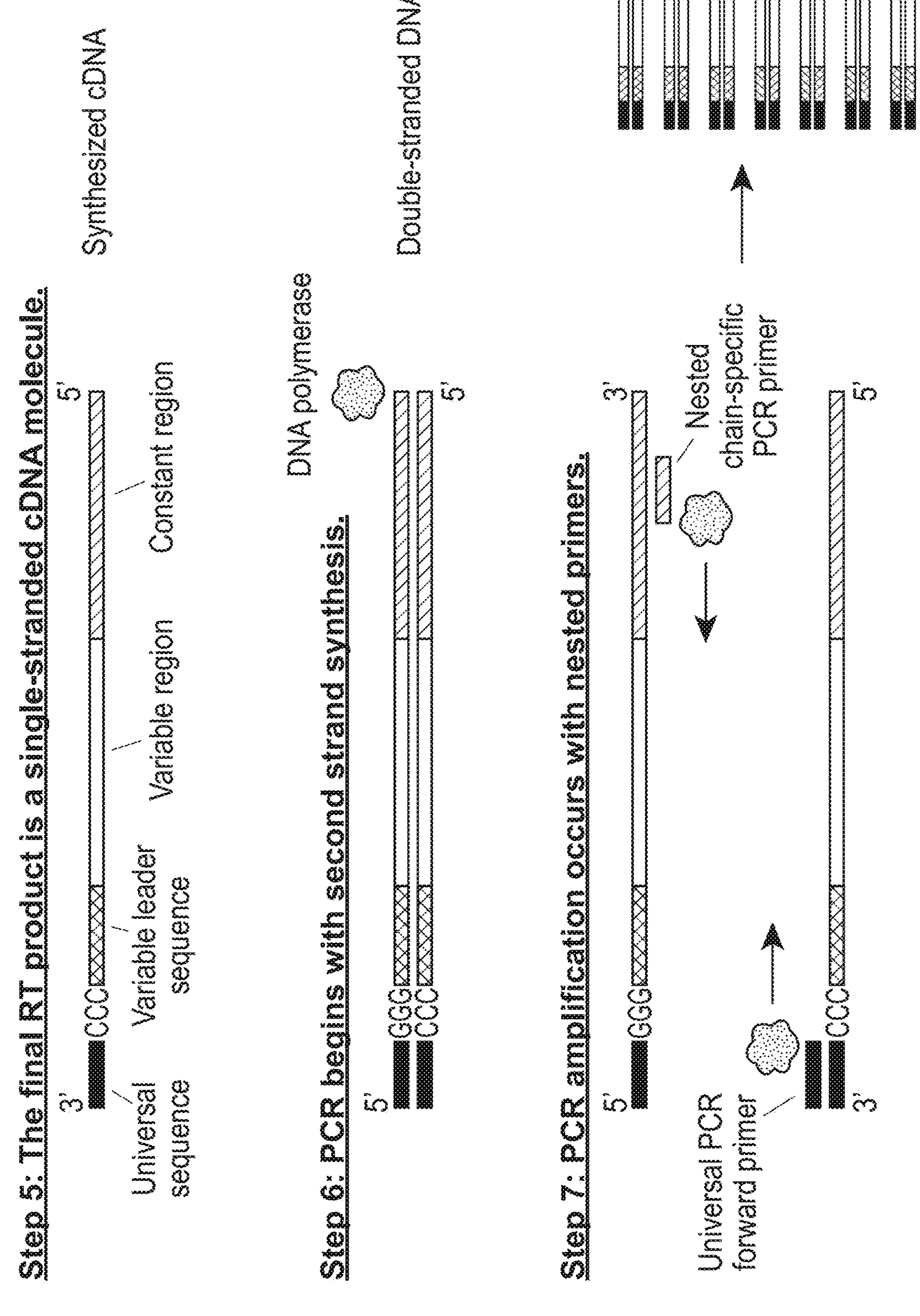

Before the methods and kits of the present disclosure are described in greater detail, it is to be understood that the methods and kits are not limited to particular embodiments described, as such may, of course, vary. It is also to be understood that the terminology used herein is for the purpose of describing particular embodiments only, and is not intended to be limiting, since the scope of the methods and kits will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods and kits. The upper and lower limits of these smaller ranges may independently be included in the smaller ranges and are also encompassed within the methods and kits, subject to any specifically excluded limit in the stated range. Where the stated range includes one or both of the limits, ranges excluding either or both of those included limits are also included in the methods and kits.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the methods and kits belong. Although any methods and kits similar or equivalent to those described herein can also be used in the practice or testing of the methods and kits, representative illustrative methods and kits are now described.

All publications and patents cited in this specification are herein incorporated by reference as if each individual publication or patent were specifically and individually indicated to be incorporated by reference and are incorporated herein by reference to disclose and describe the materials and/or methods in connection with which the publications are cited. The citation of any publication is for its disclosure prior to the filing date and should not be construed as an admission that the present methods and kits are not entitled to antedate such publication, as the date of publication provided may be different from the actual publication date which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the methods and kits, which are, for clarity, described in the context of separate embodiments, may also be provided in combination in a single embodiment. Conversely, various features of the methods and kits, which are, for brevity, described in the context of a single embodiment, may also be provided separately or in any suitable sub-combination. All combinations of the embodiments are specifically embraced by the present disclosure and are disclosed herein just as if each and every combination was individually and explicitly disclosed, to the extent that such combinations embrace operable processes and/or compositions. In addition, all sub-combinations listed in the embodiments describing such variables are also specifically embraced by the present methods and kits and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order that is logically possible.

Methods

The present disclosure provides methods of sequencing antibody chains from hybridomas. In some embodiments, the methods comprise contacting hybridoma RNA with a constant region-specific reverse transcription primer, and contacting the hybridoma RNA with a reverse transcriptase with terminal nucleotidyl transferase activity, thereby creating a heavy chain and/or light chain cDNA. Such methods further comprise contacting the heavy chain and/or light chain cDNA with a template switch oligonucleotide comprising a universal PCR primer sequence, thereby generating a heavy chain and/or light chain single stranded cDNA, and performing second strand synthesis on the heavy chain and/or light chain single stranded cDNA, thereby producing a double stranded heavy chain and/or light chain cDNA. Such methods further comprise contacting the double stranded heavy chain and/or light chain cDNA with a universal PCR primer that hybridizes to the template switch oligonucleotide and a constant region specific PCR primer, where the constant region specific PCR primer binds to a different sequence than the constant region specific reverse transcription primer, thereby producing a heavy chain and/or light chain sequencing template. Sanger sequencing is performed on the heavy chain and/or light chain sequencing template. Also provided are kits that find use, e.g., in practicing the methods of the present disclosure.

The methods of the present disclosure find use in a variety of applications. For example, the diversity of antibody variable regions makes cDNA sequencing challenging, and conventional monoclonal antibody cDNA amplification requires the use of degenerate primers. Disclosed herein is a simplified workflow for amplification of IgG antibody variable regions from hybridoma RNA by a specialized RT-PCR followed by Sanger sequencing. The method includes three separate reactions for each hybridoma: one each for kappa, lambda, and heavy chain transcripts. Reverse transcription is primed using a primer specific to each constant region. A template-switch oligonucleotide is also used to create a custom sequence at the 5' end of the antibody cDNA. Template-switching circumvents the issue of low sequence homology and the need for degenerate primers. PCR amplification of the antibody cDNA molecules uses two primers: one primer specific for the template-switch oligonucleotide sequence and a nested primer to the desired constant region.

Variable regions of five mouse monoclonal IgG antibodies have been sequenced using this method, which in turn allowed the development of chimeric mouse/human antibody expression plasmids for use in recombinant antibody production in mammalian cell culture expression systems. All five recombinant antibodies bound their respective antigens with high affinity, confirming that the amino acid sequences determined using the disclosed method are correct and demonstrating the high success rate of the disclosed method. Furthermore, RT-PCR primers were designed that amplified the variable regions of the chimeric antibodies from RNA of cells transfected with expression plasmids that express the chimeric antibodies. This shows that the disclosed method is also applicable to IgG antibodies of human origin. The disclosed monoclonal antibody sequencing method is highly accurate, user-friendly, and very cost-effective.

Disclosed herein is a robust, simple, and affordable approach to sequence monoclonal antibody variable regions from RNA with a turn-around time of five days at a cost of \$70-\$120 per antibody. Details regarding embodiments of the subject methods will now be described.

Approaches, reagents and kits for isolating ribonucleic acid (RNA) from sources of interest, e.g., hybridoma cells, are known in the art and commercially available. For example, kits for isolating nucleic acids from a source of interest include the RNeasy®, QIAamp®, QIAprep® and QIAquick® nucleic acid isolation/purification kits by Qiagen, Inc. (Germantown, Md); the ChargeSwitch®, Purelink®, GeneCatcher® nucleic acid isolation/purification kits by Life Technologies, Inc. (Carlsbad, CA); the NucleoMag®, NucleoSpin®, and NucleoBond® nucleic acid isolation/purification kits by Clontech Laboratories, Inc. (Mountain View, CA).

The methods comprise contacting hybridoma RNA with a constant region-specific reverse transcription primer. Each immunoglobulin molecule is made up of two heavy chains and two light chains joined by disulfide bonds so that each heavy chain is linked to a light chain and the two heavy chains are linked together. The amino acid sequences of many immunoglobulin heavy and light chains have been determined and reveal two important features of antibody molecules. First, each chain consists of a series of similar, although not identical, sequences, each about 110 amino acids long. Each of these repeats corresponds to a discrete, compactly folded region of protein structure known as a protein domain. The light chain is made up of two such immunoglobulin domains, whereas the heavy chain of the IgG antibody contains four. The second important feature revealed by comparisons of amino acid sequences is that the amino-terminal sequences of both the heavy and light chains vary greatly between different antibodies. The variability in sequence is limited to approximately the first 110 amino acids, corresponding to the first domain, whereas the remaining domains are constant between immunoglobulin chains of the same isotype. The amino-terminal variable or V domains of the heavy and light chains ($V_H$ and $V_L$, respectively) together make up the V region of the antibody and confer on it the ability to bind specific antigen, while the constant domains (C domains) of the heavy and light chains ($C_H$ and $C_L$, respectively) make up the C region. The multiple heavy-chain C domains are numbered from the amino-terminal end to the carboxy terminus, for example $C_H1$, $C_H2$, and so on.

Two types of light chains, termed lambda (λ) and kappa (κ), are found in antibodies. A given immunoglobulin either has κ chains or λ chains, never one of each. No functional difference has been found between antibodies having λ or κ light chains, and either type of light chain may be found in antibodies of any of the five major classes. The ratio of the two types of light chain varies from species to species. There are five main heavy-chain classes or isotypes, some of which have several subtypes, and these determine the functional activity of an antibody molecule. The five major classes of immunoglobulin are immunoglobulin M (IgM), immunoglobulin D (IgD), immunoglobulin G (IgG), immunoglobulin A (IgA), and immunoglobulin E (IgE). Their heavy chains are denoted by the corresponding lower-case Greek letter (μ, δ, γ, α, and ε, respectively). IgG is by far the most abundant immunoglobulin and has several subclasses (IgG1, 2, 3, and 4 in humans). Their distinctive functional properties are conferred by the carboxy-terminal part of the heavy chain, where it is not associated with the light chain. The general structural features of all the isotypes are similar.

The methods utilize the ability of certain nucleic acid polymerases to "template switch," using a first nucleic acid strand as a template for polymerization, and then switching to a second template nucleic acid strand (which may be referred to as a "template switch nucleic acid" or an "acceptor template") while continuing the polymerization reaction. The result is the synthesis of a hybrid nucleic acid strand with a 5' region complementary to the first template nucleic acid strand and a 3' region complementary to the template switch nucleic acid.

As set forth above, the subject methods comprise contacting the heavy chain and/or light chain cDNA with a template switch oligonucleotide. By "template switch oligonucleotide" is meant an oligonucleotide template to which a polymerase switches from an initial template (e.g., the template nucleic acid in the subject methods) during a nucleic acid polymerization reaction. In this regard, the template nucleic acid may be referred to as a "donor template" and the template switch oligonucleotide may be referred to as an "acceptor template." As used herein, an "oligonucleotide" is a single-stranded multimer of nucleotides from 2 to 500 nucleotides, e.g., 2 to 200 nucleotides. Oligonucleotides may be synthetic or may be made enzymatically, and, in some embodiments, are 5 to 50 nucleotides in length (e.g., 9 to 50 nucleotides in length). Oligonucleotides may contain ribonucleotide monomers (i.e., may be oligoribonucleotides or "RNA oligonucleotides") or deoxyribonucleotide monomers (i.e., may be oligodeoxyribonucleotides or "DNA oligonucleotides"). Oligonucleotides may be 5 to 9, 10 to 20, 21 to 30, 31 to 40, 41 to 50, 51 to 60, 61 to 70, 71 to 80, 80 to 100, 100 to 150 or 150 to 200, up to 500 or more nucleotides in length, for example.

According to some embodiments, the template switch oligonucleotide comprises aagcagtggtatcaacgcagagtacatg$_r$g$_r$g$_r$ (SEQ ID NO:1) and where the universal forward primer comprises aagcagtggtatcaacgcagag (SEQ ID NO:5) or a variant thereof wherein any variant is at least 90% identical to the original sequence.

Antibody constant region amino acid sequences are known. Based on these known sequences, a variety of different constant region-specific reverse transcription primers may be designed and employed for practicing the methods of the present disclosure. Such primers are capable of specifically hybridizing to all or a portion of a constant region of interest. Whether specific hybridization occurs is determined by such factors as the degree of complementarity between the relevant (that is, hybridizing) region of a primer and the target RNA or cDNA, etc., as well as the length thereof, salt concentration, and the temperature at which the hybridization occurs, which may be informed by the melting temperatures ($T_M$) of the relevant regions. The melting temperature refers to the temperature at which half of the relevant regions remain hybridized and half of the relevant regions dissociate into single strands. The Tm of a duplex may be experimentally determined or predicted using the following formula $Tm=81.5+16.6(\log 10[Na^+])+0.41$ (fraction G+C)−(60/N), where N is the chain length and $[Na^+]$ is less than 1 M. See Sambrook and Russell (2001; Molecular Cloning: A Laboratory Manual, 3rd ed., Cold Spring Harbor Press, Cold Spring Harbor N.Y., Ch. 10). Other more advanced models that depend on various parameters may also be used to predict Tm of complementarity region/overhang duplexes depending on various hybridization conditions. Approaches for achieving specific nucleic acid hybridization may be found in, e.g., Tijssen, Laboratory Techniques in Biochemistry and Molecular Biology-Hybridization with Nucleic Acid Probes, part I, chapter 2, “Overview of principles of hybridization and the strategy of nucleic acid probe assays,” Elsevier (1993).

Non-limiting examples of constant region-specific reverse transcription primers and PCR primers that may be employed when practicing the methods of the present disclosure include, but are not limited to, primers comprising, consisting essentially of, or consisting of a nucleotide sequence of a primer set forth in Table 1 or Table 2 below, or a nucleotide sequence having 90% or greater, or 95% or greater nucleotide sequence identity to a nucleotide sequence of a primer set forth in Table 1 or Table 2 below.

The contacting steps are performed under conditions sufficient to produce the desired nucleic acid, e.g., conditions that permit polymerase-mediated extension of a 3' end of a primer, template switching of the polymerase to the template switch oligonucleotide, continuation of the extension reaction using the template switch oligonucleotide as the template. Achieving suitable reaction conditions may include selecting reaction mixture components, concentrations thereof, and a reaction temperature to create an environment in which the polymerase is active and the relevant nucleic acids in the reaction interact (e.g., hybridize) with one another in the desired manner. For example, in addition to the primer(s), the polymerase, the template, dNTPs, etc., the reaction mixture may include buffer components that establish an appropriate pH, salt concentration (e.g., KCl concentration), metal cofactor concentration (e.g., $Mg^{2+}$ or $Mn^{2+}$ concentration), and the like, for the extension reaction and template switching to occur. Other components may be included, such as one or more nuclease inhibitors (e.g., an RNase inhibitor and/or a DNase inhibitor). The reaction mixture can have a pH suitable for the reverse transcription, etc. According to some embodiments, the pH of the reaction mixture ranges from 5 to 9, such as from 7 to 9, including from 8 to 9, e.g., 8 to 8.5.

In some embodiments, one or more primers, template switch oligonucleotides, and/or the like comprise one or more non-natural nucleotides (which may also be referred to as nucleotide analogs). Non-limiting examples of non-natural nucleotides of interest include LNA (locked nucleic acid), PNA (peptide nucleic acid), FANA (2'-deoxy-2'-fluoroarabinonucleotide), GNA (glycol nucleic acid), TNA (threose nucleic acid), 2'-O-Me RNA, 2'-fluoro RNA, Morpholino nucleotides, and any combination thereof.

In some embodiments, one or more primers, template switch oligonucleotides, and/or the like include one or more labels. Labels of interest include, e.g., detectable labels. As used herein, a “detectable label” is a chemical moiety that affords detectability to a species (e.g., oligonucleotide) attached thereto. Exemplary detectable labels include fluorescent labels, luminescent labels, radioactive labels, spectroscopic labels, stable isotope mass tagged labels, electron spin resonance labels, nuclear magnetic resonance labels, chelated metal labels, and the like.

In some embodiments, one or more primers, template switch oligonucleotides, and/or the like include one or more affinity tags. The term “affinity tag,” as used herein, refers to a chemical moiety that functions as, or contains, an affinity ligand that is capable of binding (e.g., non-covalently or covalently) to a second, “capture” chemical moiety, such that the nucleic acid complex or derivative thereof can be selected (or “captured”) from a mixture using the capture moiety. In some embodiments, the capture moiety is bound to a solid support, e.g., a bead (e.g., a magnetic bead), planar surface, or the like. Non-limiting examples of affinity tags that may be employed include biotin, avidin, streptavidin, an aptamer (see, e.g., Wilson & Szostak (1999) *Annu Rev Biochem.* 68:611-647), an MS2 coat protein-interacting sequence, a U1A protein-interacting sequence, etc. Nucleic acid affinity tags that find use in the one or more primers, template switch oligonucleotides, and/or the like are described, e.g., in Walker et al. (2008) *Methods Mol Biol.* 488:23-40. Interactions between the affinity tag and the capture moiety may be specific and reversible (e.g., non-covalent binding or hydrolyzable covalent linkage), but if desired, may be (or subsequently may be made) irreversible, e.g., a non-hydrolyzable covalent linkage between the affinity tag and the capture moiety.

The methods of the present disclosure include performing Sanger sequencing on the heavy chain and/or light chain sequencing template. Sanger sequencing is a method of DNA sequencing based on the selective incorporation of chain-terminating nucleotides (e.g., dideoxynucleotides) by a polymerase during in vitro DNA replication. It has the advantage over short-read sequencing technologies (like Illumina) in that it can produce DNA sequence reads of >500 nucleotides. The classical chain-termination method requires a single-stranded DNA template, a DNA primer, a DNA polymerase, normal deoxynucleotidetriphosphates (dNTPs), and modified di-deoxynucleotidetriphosphates (ddNTPs), the latter of which terminate DNA strand elongation. These chain-terminating nucleotides lack a 3'-OH group required for the formation of a phosphodiester bond between two nucleotides, causing DNA polymerase to cease extension of DNA when a modified ddNTP is incorporated. The ddNTPs may be radioactively or fluorescently labelled for detection in automated sequencing machines.

The DNA sample is divided into four separate sequencing reactions, containing all four of the standard deoxynucleotides (dATP, dGTP, dCTP and dTTP) and the DNA polymerase. To each reaction is added only one of the four dideoxynucleotides (ddATP, ddGTP, ddCTP, or ddTTP), while the other added nucleotides are ordinary ones. The dideoxynucleotide concentration should be approximately 100-fold higher than that of the corresponding deoxynucleotide (e.g. 0.5 mM ddTTP: 0.005 mM dTTP) to allow enough fragments to be produced while still transcribing the complete sequence (but the concentration of ddNTP also depends on the desired length of sequence). Putting it in a more sensible order, four separate reactions are needed in this process to test all four ddNTPs. Following rounds of template DNA extension from the bound primer, the resulting DNA fragments are heat denatured and separated by size using gel electrophoresis. The DNA bands may then be visualized by autoradiography or UV light and the DNA sequence can be directly read off the X-ray film or gel image.

Automated DNA-sequencing instruments (DNA sequencers) can sequence, e.g., 384 DNA samples in a single batch. DNA sequencers separate strands by size (or length) using capillary electrophoresis, they detect and record dye fluorescence, and output data as fluorescent peak trace chromatograms. Sequencing reactions (thermocycling and labelling), cleanup and re-suspension of samples in a buffer solution are performed separately, before loading samples onto the sequencer. A number of commercial and non-commercial software packages can trim low-quality DNA traces automatically. These programs score the quality of each peak and remove low-quality base peaks (which are generally located at the ends of the sequence). The accuracy of such algorithms is adequate for automated processing of large sequence data sets.

Further details regarding Sanger sequencing are available in the literature, including but not limited to, Smith et al. (1986) "Fluorescence detection in automated DNA sequence analysis" *Nature* 321(6071): 674-9.

Kits

Also provided are kits. In certain embodiments, provided our kits comprising a first mixture comprising an IgG constant region reverse transcription primer, an IgK constant region reverse transcription primer, and an IgL constant region reverse transcription primer. Such kits further comprise a second mixture comprising an IgG constant region PCR primer, an IgK constant region PCR primer, and an IgL constant region PCR primer. Such kits may further include instructions for performing any of the methods of the present disclosure.

According to some embodiments, the IgG constant region reverse transcription primer, IgK constant region reverse transcription primer, IgL constant region reverse transcription primer, IgG constant region PCR primer, IgK constant region PCR primer, and IgL constant region PCR primer are specific for mouse IgG, IgK, and IgL. In certain embodiments, the IgG constant region reverse transcription primer comprises agctgggaaggtgtgcacac (SEQ ID NO:4) or a variant thereof, where the IgK constant region reverse transcription primer comprises ttgtcgttcactgccatcaatc (SEQ ID NO:2) or a variant thereof, where the IgL constant region reverse transcription primer comprises ggggtaccatctaccttccag (SEQ ID NO:3) or a variant thereof, where the IgG constant region PCR primer comprises gggatccagagttccaggtc (SEQ ID NO:8) or a variant thereof, where the IgK constant region PCR primer comprises acattgatgtctttggggtagaag (SEQ ID NO:6) or a variant thereof, and where the IgL constant region PCR primer comprises atcgtacacaccagtgtggc (SEQ ID NO:7) or a variant thereof and where any variant is at least 90% identical to the original sequence.

In certain embodiments, the IgG constant region reverse transcription primer, IgK constant region reverse transcription primer, IgL constant region reverse transcription primer, IgG constant region PCR primer, IgK constant region PCR primer, and IgL constant region PCR primer are specific for human IgG, IgK, and IgL. According to some embodiments, the IgG constant region reverse transcription primer comprises gccgggaaggtgtgcacg (SEQ ID NO:10) or a variant thereof, where the IgK constant region reverse transcription primer comprises gattggagggcgttatccacc (SEQ ID NO:9) or a variant thereof where the IgG constant region PCR primer comprises agggcgcctgagttccacg (SEQ ID NO:12) or a variant thereof, and where the IgK constant region PCR primer comprises tttggcctctctgggatagaag (SEQ ID NO:11) or a variant thereof, and where any variant is at least 90% identical to the original sequence.

Components of the kits may be present in separate containers, or multiple components may be present in a single container. Suitable containers include tubes, vials, and/or the like.

In addition to the above-mentioned components, and as described above, a subject kit may further include instructions for using the components of the kit, e.g., to practice the methods of the present disclosure, e.g., for using the first and second mixtures to sequence an antibody heavy chain or light chain from a hybridoma. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, Hard Disk Drive (HDD) etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Notwithstanding the appended claims, the present disclosure is also defined by the following embodiments:

1. A method of sequencing an antibody heavy chain or light chain from a hybridoma, the method comprising:

contacting hybridoma RNA with a constant region-specific reverse transcription primer;

contacting the hybridoma RNA with a reverse transcriptase with terminal nucleotidyl transferase activity, thereby creating a heavy chain and/or light chain cDNA;

contacting the heavy chain and/or light chain cDNA with a template switch oligonucleotide comprising a universal PCR primer sequence, thereby generating a heavy chain and/or light chain single stranded cDNA;

performing second strand synthesis on the heavy chain and/or light chain single stranded cDNA, thereby producing a double stranded heavy chain and/or light chain cDNA;

contacting the double stranded heavy chain and/or light chain cDNA with a universal PCR primer that hybridizes to the template switch oligonucleotide and a constant region specific PCR primer, where the constant region specific PCR primer binds to a different sequence than the constant region specific reverse transcription primer, thereby producing a heavy chain and/or light chain sequencing template;

performing Sanger sequencing on the heavy chain and/or light chain sequencing template.

2. The method according to embodiment 1, wherein the template switch oligonucleotide comprises aagcagtggtatcaacgcagagtacatg$_r$g$_r$g$_r$ a (SEQ ID NO:1) and where the universal forward primer comprises aagcagtggtatcaacgcagag (SEQ ID NO:5) or a variant thereof wherein any variant is at least 90% identical to the original sequence.

3. The method according to embodiment 1, wherein the hybridoma comprises a mouse constant region.

4. The method according to embodiment 3, further comprising contacting the hybridoma RNA with an IgG constant region reverse transcription primer and a second primer that is an IgK constant region reverse transcription primer or an IgL constant region reverse transcription primer.

5. The method according to embodiment 4, further comprising contacting the hybridoma RNA with an IgG constant region reverse transcription primer, an IgK constant region reverse transcription primer and an IgL constant region reverse transcription primer.

6. The method according to embodiment 4, wherein the IgG constant region reverse transcription primer comprises agctgggaaggtgtgcacac (SEQ ID NO:4) or a variant thereof, where the IgK constant region reverse transcription primer comprises ttgtcgttcactgccatcaatc (SEQ ID NO:2) or a variant thereof, and where the IgL constant region reverse transcription primer comprises ggggtaccatctaccttccag (SEQ ID NO:3) or a variant thereof, where any variant is at least 90% identical to the listed sequence.

7. The method according to embodiment 3, further comprising contacting the double stranded heavy chain and/or light chain cDNA with an IgG constant region PCR primer and a second primer that is an IgK constant region PCR primer or an IgL constant region PCR primer.

8. The method according to embodiment 7, further comprising contacting the double stranded heavy chain and/or light chain cDNA with an IgG constant region PCR primer, an IgK constant region PCR primer, and an IgL constant region PCR primer.

9. The method according to embodiment 7, wherein the IgG constant region PCR primer comprises gggatccagagttccaggtc (SEQ ID NO:8) or a variant thereof, where the IgK constant region PCR primer comprises acattgatgtctttggggtagaag (SEQ ID NO:6) or a variant thereof, and where the IgL constant region PCR primer comprises atcgtacacaccagtgtggc (SEQ ID NO:7) or a variant thereof where any variant is at least 90% identical to the listed sequence.

10. The method according to embodiment 1, wherein the hybridoma comprises a human constant region.

11. The method according to embodiment 10, further comprising contacting the hybridoma RNA with an IgG constant region reverse transcription primer and a second primer that is an IgK constant region reverse transcription primer or an IgL constant region reverse transcription primer.

12. The method according to embodiment 11, further comprising contacting the hybridoma RNA with an IgG constant region reverse transcription primer, an IgK constant region reverse transcription primer and an IgL constant region reverse transcription primer.

13. The method according to embodiment 11, wherein the IgG constant region reverse transcription primer comprises gccgggaaggtgtgcacg (SEQ ID NO:10) or a variant thereof and the IgK constant region reverse transcription primer comprises gattggagggcgttatccacc (SEQ ID NO:9) or a variant thereof where any variant is at least 90% identical to the listed sequence.

14. The method according to embodiment 10, comprising contacting the double stranded heavy chain and/or light chain cDNA with an IgG constant region PCR primer and a second primer that is an IgK constant region PCR primer or an IgL constant region PCR primer.

15. The method according to embodiment 14, comprising contacting the double stranded heavy chain and/or light chain cDNA with an IgG constant region PCR primer, an IgK constant region PCR primer, and an IgL constant region PCR primer.

16. The method according to embodiment 14, wherein the IgG constant region PCR primer comprises agggcgcctgagttccacg (SEQ ID NO:12) or a variant thereof and where the IgK constant region PCR primer comprises tttggcctctctgggatagaag (SEQ ID NO:11) or a variant thereof, where the variant is at least 90% identical to the listed sequence.

17. The method according to embodiment 1, wherein the reverse transcriptase is an MMLV reverse transcriptase.

18. A kit comprising:

a first mixture comprising an IgG constant region reverse transcription primer, an IgK constant region reverse transcription primer, and an IgL constant region reverse transcription primer; and a second mixture comprising an IgG constant region PCR primer, an IgK constant region PCR primer, and an IgL constant region PCR primer.

19. The kit of embodiment 18, wherein the IgG constant region reverse transcription primer, IgK constant region reverse transcription primer, IgL constant region reverse transcription primer, IgG constant region PCR primer, IgK constant region PCR primer, and IgL constant region PCR primer are specific for mouse IgG, IgK, and IgL.

20. The kit of embodiment 19, wherein the IgG constant region reverse transcription primer comprises agctgggaaggtgtgcacac (SEQ ID NO:4) or a variant thereof, where the IgK constant region reverse transcription primer comprises ttgtcgttcactgccatcaatc (SEQ ID NO:2) or a variant thereof, where the IgL constant region reverse transcription primer comprises ggggtaccatctaccttccag (SEQ ID NO:3) or a variant thereof, where the IgG constant region PCR primer comprises gggatccagagttccaggtc (SEQ ID NO:8) or a variant thereof, where the IgK constant region PCR primer comprises acattgatgtctttggggtagaag (SEQ ID NO:6) or a variant thereof, and where the IgL constant region PCR primer comprises atcgtacacaccagtgtggc (SEQ ID NO:7) or a variant thereof and where any variant is at least 90% identical to the original sequence.

21. The kit of embodiment 18, wherein the IgG constant region reverse transcription primer, IgK constant region reverse transcription primer, IgL constant region reverse transcription primer, IgG constant region PCR primer, IgK constant region PCR primer, and IgL constant region PCR primer are specific for human IgG, IgK, and IgL.

22. The kit of embodiment 21, wherein the IgG constant region reverse transcription primer comprises gccgggaaggtgtgcacg (SEQ ID NO:10) or a variant thereof, where the IgK constant region reverse transcription primer comprises gattggagggcgttatccacc (SEQ ID NO:9) or a variant thereof where the IgG constant region PCR primer comprises agggcgcctgagttccacg (SEQ ID NO:12) or a variant thereof, and where the IgK constant region PCR primer comprises tttggcctctctgggatagaag (SEQ ID NO:11) or a variant thereof, and where any variant is at least 90% identical to the original sequence.

The following examples are offered by way of illustration and not by way of limitation.

EXPERIMENTAL

Example 1—Monoclonal Antibody Sequencing Strategy

To sequence the variable regions of five mouse monoclonal IgG1 antibodies (2D9, 3B4, 3E8, 3H4, and 4B6), (Reference 26) total RNA was extracted from each hybridoma cell line a modified RT-PCR (reverse transcription polymerase chain reaction) applied using SMART (switching mechanism at 5' end of RNA transcript) technology. (References 27,28). This technology is based on the intrinsic features of the reverse transcriptase from the Moloney murine leukemia virus (MMLV) and the application of a custom-sequence template-switch oligonucleotide (template-switch oligo) forward primer containing 3 riboguanines (rGrGrG) at its 3' end. To amplify antibody variable regions, RT-PCR reverse primers were designed to be specific for highly conserved sequences in the constant regions of kappa, lambda, and IgG heavy chains of mouse antibodies (Tables 1 and 2).

of the RNA template during first strand synthesis, it adds several nucleotides, usually deoxycytosine, to the 3' end of the cDNA transcript (FIG. 1, Step 2). The reliable addition of these bases by the MMLV reverse transcriptase allows annealing of the template-switch oligonucleotide (Table 1).

When base pairing occurs between the template-switch oligo's 3' riboguanines and the cDNA deoxycytosine overhang (FIG. 1, Step 3), the MMLV reverse transcriptase switches templates and continues polymerization, now using the template-switch oligonucleotide as the template rather than the hybridoma RNA, until it reaches the 5' end of the template-switch oligonucleotide (FIG. 1, Step 4). The final product is a single-stranded cDNA molecule containing an initial universal sequence added by the template-switch oligonucleotide followed by the complete 5' to 3' sequence of the RNA template region (FIG. 1, Step 5). This cDNA becomes the template for second-strand synthesis (FIG. 1, Step 6) and amplification in PCR (FIG. 1, Step 7) by taking advantage of the added universal sequence. The forward PCR primer (Table 2) has the same sequence as the template-switch oligonucleotide and therefore binds the universal sequence added to the cDNA transcript during reverse transcription. The reverse PCR primers (Table 2) are again specific for each chain's constant region at a second highly conserved sequence but are nested within the cDNA

TABLE 1

Mouse IgG reverse transcription primers.

| Primer Name | Forward or Reverse | Primer Sequence |
|---|---|---|
| Template-switch oligo | Universal forward primer | 5' aagcagtggtatcaacgcagagtacatgrgrgr 3' (SEQ ID NO: 1) |
| mIGK RT | Reverse primer for kappa chain | 5' ttgtcgttcactgccatcaatc 3' (SEQ ID NO: 2) |
| mIGL RT | Reverse primer for lambda chain | 5' ggggtaccatctaccttccag 3' (SEQ ID NO: 3) |
| mIGHG RT | Reverse primer for heavy chain | 5' agctgggaaggtgtgcacac 3' (SEQ ID NO: 4) |

TABLE 2

Mouse IgG PCR primers.

| Primer Name | Forward or Reverse | Primer Sequence |
|---|---|---|
| ISPCR | Universal forward primer | 5' aagcagtggtatcaacgcagag 3' (SEQ ID NO: 5) |
| mIGK PCR | Reverse primer for kappa chain | 5' acattgatgtctttggggtagaag 3' (SEQ ID NO: 6) |
| mIGL PCR | Reverse primer for lambda chain | 5' atcgtacacaccagtgtggc 3' (SEQ ID NO: 7) |
| mIGHG PCR | Reverse primer for heavy chain | 5' gggatccagagttccaggtc 3' (SEQ ID NO: 8) |

The RT-PCR amplification of antibody variable regions occurs as follows: To begin reverse transcription of a particular variable region, the reverse transcription primer specific for that antibody chain (either kappa, lambda, or heavy; Table 1) binds the hybridoma RNA within the constant region sequence at a highly conserved site. The MMLV reverse transcriptase initiates polymerization (FIG. 1, Step 1). After the MMLV reverse transcriptase reaches the 5' end sequence synthesized during reverse transcription to promote amplification specificity.

Referring now to FIG. 1: Step 1 shows primer binding and initiation of polymerization. Step 2 shows that MMLV reverse transcriptase adds deoxycytosines to the cDNA 3' end. Step 3 shows that the template-switch oligonucleotide binds the CCC overhang. Step 4 shows that the reverse transcriptase switches templates and continues polymerization using the template-switch oligonucleotide as the template. Steps 5-7 show the single-stranded cDNA product of reverse transcription becomes the template for second-strand synthesis primed by the universal PCR forward primer. Amplification follows using the universal PCR forward primer and nested chain-specific PCR reverse primers. Note that the lengths of the different antibody regions and primers are not to scale.

A total of fifteen total RT-PCR reactions were set up: five hybridoma RNA samples with three RT-PCR reactions each to amplify kappa, lambda, and heavy chain variable regions. Kappa and lambda chain amplifications were set up for each antibody because the light chain used in each hybridoma was unknown. The reactions were confirmed by agarose gel electrophoresis. After optimizing primer design (see below), four of the five samples showed amplification of kappa chains. The 3H4 showed amplifications of both kappa and lambda chains, and all samples showed amplification of heavy chains. Each amplicon is 550-600 base pairs in size (FIG. 2B).

Example 2—Primer Selection

To optimize RT-PCR amplification of the variable regions of mouse kappa, lambda, and IgG heavy chains, multiple sets of primers were designed and tested. Two strategies of primer selection were followed. For both strategies, the RT was performed using a template-switch oligonucleotide forward primer and reverse transcription primers specific for kappa, lambda, or heavy chain constant regions. These are referred to as mIGK RT, mIGL RT, and mIGHG RT, respectively (Table 1). Strategies for selecting primers to perform PCR amplification were also assessed. In one strategy, the same reverse primers for both RT and PCR were used—i.e. in the PCR step, the ISPCR forward primer (Table 2, Row 1), which has the same 5' sequence as the template-switch oligonucleotide was used as the forward primer and the mIGK RT, mIGL RT, or mIGHG RT oligos were used as reverse primers (Table 1).

For another primer strategy, the reverse PCR primers were nested within the sequence created by reverse transcription to promote specificity for the desired variable region amplicon (FIG. 1, Step 7). So in this case, the ISPCR forward primer was used as the forward primer and the nested reverse primers mIGK PCR, mIGL PCR, or mIGHG PCR (Table 2) were used as the reverse primer.

Figure 2:
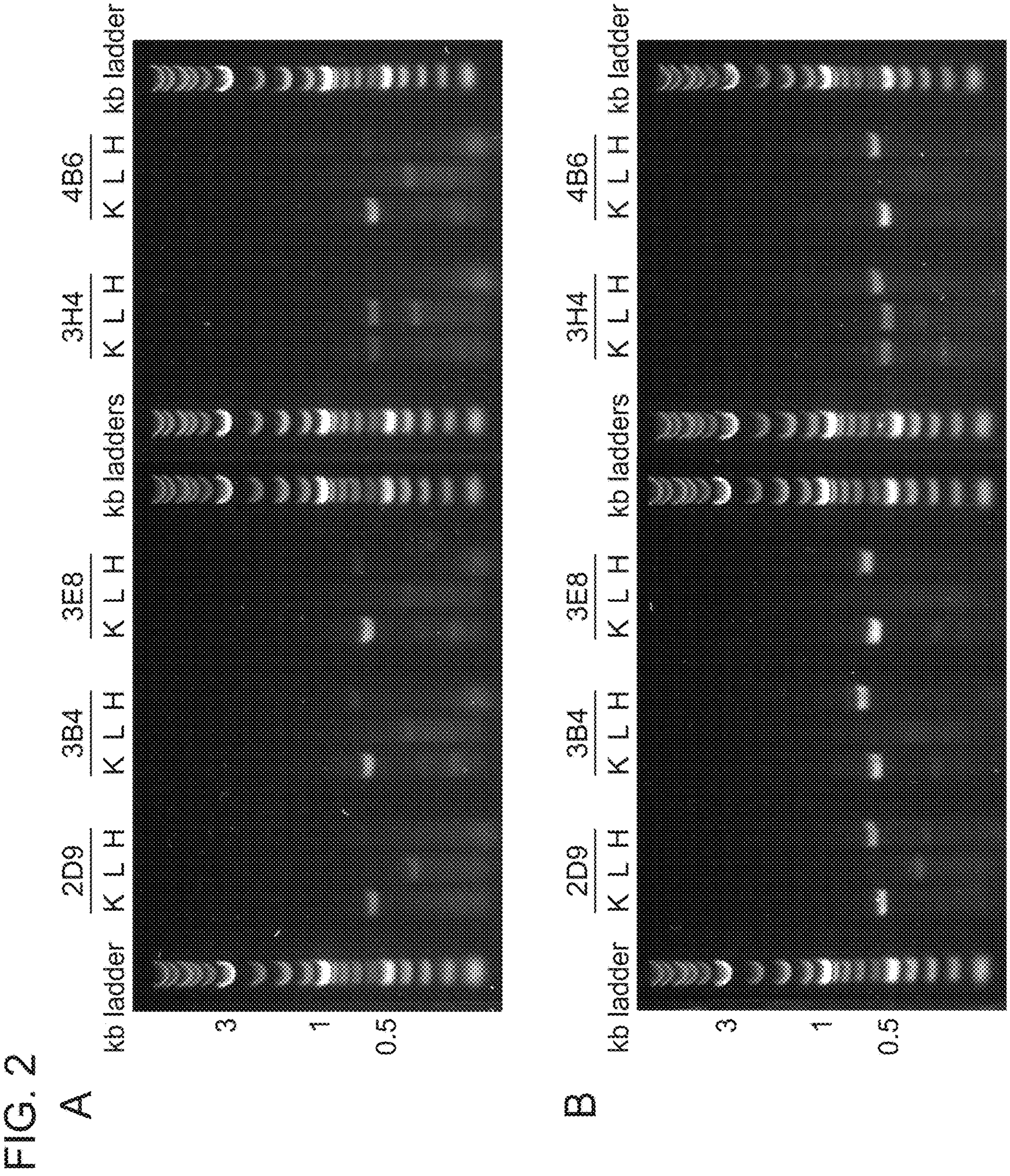
FIG. 2A-2B: A comparison of primer sets for RT-PCR amplification of variable regions from 5 hybridoma mRNA samples.

Referring now to FIG. 2 where RT-PCR results obtained using primers selected by the above strategies were performed. Comparing results of PCR using the same reverse primers for RT and for PCR (FIG. 2A) to the results obtained using nested primers (FIG. 2B) clearly shows that nested primers produce more efficient amplification of antibody variable regions. In particular, the heavy chains of each antibody did not amplify, or only amplified faintly, using the same reverse primers in RT and PCR but amplified well when choosing nested primers for PCR. In addition, using nested primers increased the intensity of the kappa amplification product for each antibody. Finally, use of the nested primers led to a reduction in intensity or even elimination of a ~350 base pair non-specific lambda chain amplicon. Therefore, nested primers should be used for monoclonal antibody sequencing.

A Clustal Omega (Reference 29) multiple sequence alignment (not shown) of the constant regions from all subclasses of mouse IgG (IgG1, IgG2a, IgG2b, IgG2c, and IgG3) was performed using sequences available on IMGT, the international ImMunoGeneTics information system. (Reference 30) Based on the alignment, the mIGHG RT and mIGHG PCR were hypotheisized to prime from the constant regions of IgG1, IgG2a, IgG2b, and IgG2c antibodies but likely not to prime from the constant region of IgG3 antibodies because of five mismatches to each primer. The primers given in Tables 1 and 2 may then be used to sequence antibodies from the majority of all mouse IgG subclasses.

Example 3—Sequencing Results

Following RT-PCR, the amplicons were purified by agarose gel extraction and directly sequenced by Sanger sequencing to determine the variable region sequences of the light and heavy chains from all five antibodies. The sequencing data were analyzed with a custom Python program available on GitHub. The sequences of one kappa and three heavy chains were analyzed in this manner (Table 3 under Number of Amplicons Sequenced). However, the sequencing data was not clear enough to determine the remaining sequences. Therefore, a sequencing vector was used to improve the quality of the DNA sequenced. RT-PCR products were purified with a PCR clean-up kit, blunt-end cloned into a plasmid, transformed into *E. coli*, and the plasmid clones sequenced using Sanger sequencing. Clear sequencing data was obtained for plasmid clones from each of the variable regions (Table 3). This result is an improvement on the outcome of direct PCR sequencing, which only positively identified four variable regions. A sufficient number of plasmid clones of each light and heavy chain variable region were sequenced to compare at least three amino acid sequences of each variable region to confirm sequence identity (Table 3 under Number of Plasmid Clones Sequenced). Clustal Omega was used for these alignments (not shown).

TABLE 3

Results of sequencing RT-PCR products directly and following blunt-end cloning.

| | Number of Amplicons Sequenced | | | Number of Plasmid Clones Sequenced | | |
|---|---|---|---|---|---|---|
| Antibody | Total | Amplicons Containing Light Chain | Amplicons Containing Heavy Chain | Total | Clones Containing Light Chain | Clones Containing Heavy Chain |
| 2D9 | 6 | 0 | 3 | 20 | 3 | 4 |
| 3B4 | 6 | 0 | 0 | 10 | 4 | 3 |
| 3E8 | 6 | 3 | 0 | 20 | 5 | 3 |
| 3H4 | 6 | 0 | 3 | 15 | 5 | 4 |
| 4B6 | 6 | 0 | 3 | 18 | 3 | 3 |

Once a consensus sequence for each of the ten variable regions was identified, the IgBLAST tool, (Reference 31) a tool for alignment of immunoglobulin and T cell receptor variable domain sequences, was used to determine the percent identity of the light and heavy chain variable regions to IgBLAST reference sequences, i.e. the top-matched germline V genes. Table 4 shows the results of this query. The percent identity to the reference of each frame region and complementarity-determining region (CDR) of each antibody's light and heavy chain ranged from 87.5% to 100%. All regions of 3E8 kappa, 4B6 kappa, 2D9 heavy, and 3E8 heavy chains matched 100% to the reference sequences. For light chains, the average percent identity of all frame regions and CDRs to the references was 99.2%. For heavy chains, the average percent identity of all frame regions and CDRs to the references was 98%. These results support the conclusion that the sequences determined with the disclosed method are viable antibodies from hybridoma RNA.

TABLE 4

Percent identity to IgBLAST reference sequences.

| Antibody | Frame Region 1 | Frame Region 2 | Frame Region 3 | CDR 1 | CDR 2 | CDR 3 | Total |
|---|---|---|---|---|---|---|---|
| | Percent Identity of Light Chain to IgBLAST References | | | | | | |
| 2D9 | 100% | 100% | 100% | 94.4% | 100% | 100% | 99.7% |
| 3B4 | 100% | 98% | 99.1% | 100% | 88.9% | 90% | 98.2% |
| 3E8 | 100% | 100% | 100% | 100% | 100% | 100% | 100% |
| 3H4 | 100% | 96.1% | 98.1% | 100% | 100% | 95.5% | 98.3% |
| 4B6 | 100% | 100% | 100% | 100% | 100% | 100% | 100% |
| Average | 100% | 98.8% | 99.4% | 98.9% | 97.8% | 97.1% | 99.2% |
| | Percent Identity of Heavy Chain to IgBLAST References | | | | | | |
| 2D9 | 100% | 100% | 100% | 100% | 100% | 100% | 100% |
| 3B4 | 97.3% | 100% | 94.7% | 100% | 91.7% | — | 96.5% |
| 3E8 | 100% | 100% | 100% | 100% | 100% | 100% | 100% |
| 3H4 | 98.7% | 96.1% | 92.1% | 91.7% | 90.5% | 87.5% | 94.2% |
| 4B6 | 100% | 100% | 99.1% | 100% | 95.2% | 100% | 99.3% |
| Average | 99.2% | 99.2% | 97.2% | 98.3% | 95.5% | 96.9% | 98% |

The percent identity of each region is reported as given by IgBLAST. The total percent identity was calculated by IgBLAST as the number of matches between the query and reference sequences over the length of the aligned sequence multiplied by 100. The averages refer to the average of all values in that column.

Figure 3:
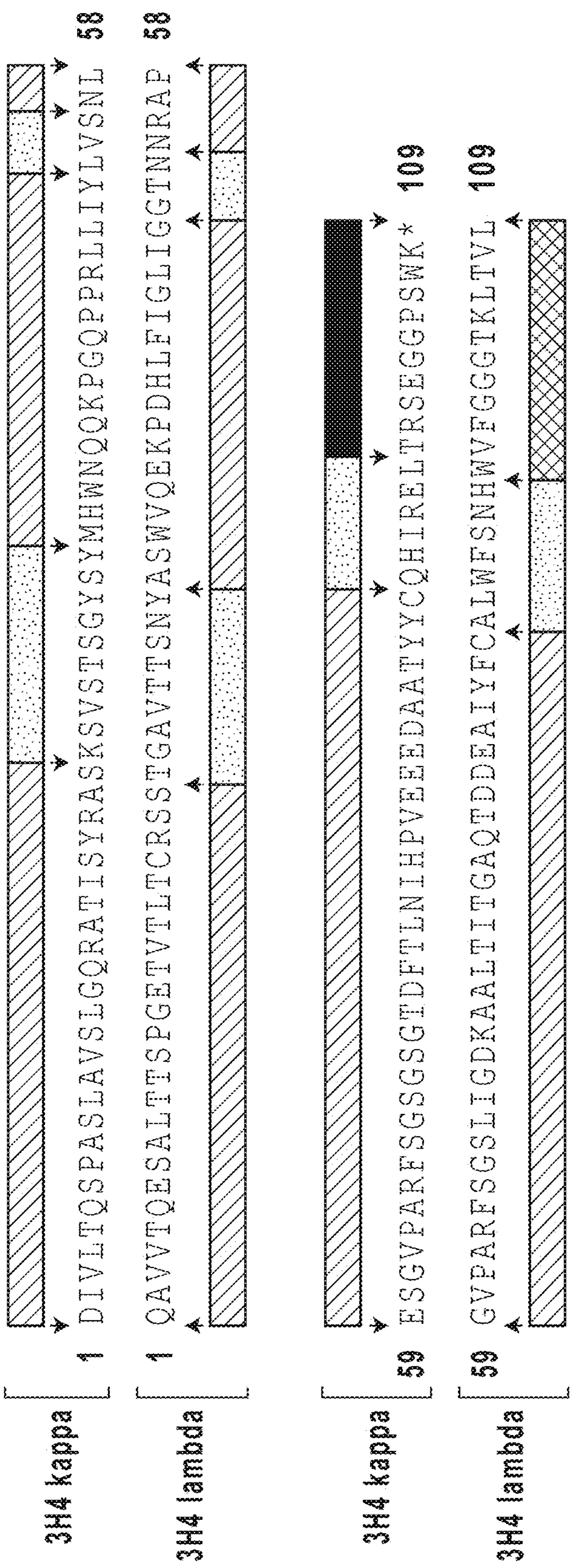
FIG. 3: A protein sequence comparison of variable regions for 3H4 kappa (top—SEQ ID NO: 13) and 3H4 lambda (bottom—SEQ ID NO: 14). Blue=Frame region, Orange=Complementarity-determining region, Red=J region out-of-frame, Green=J region in-frame 3H4 kappa (top) has an early stop codon due to a frameshift mutation. 3H4 lambda (bottom) is full-length.

Because amplification of both the kappa and lambda chains occurred for 3H4, as opposed to amplification of only one of the light chains as for the other four antibodies (FIG. 2B), the amplicons were purified, blunt-end cloned, and the RT-PCR products sequenced for both 3H4 kappa and 3H4 lambda. Sequencing revealed that the 3H4 kappa variable region contains a frameshift mutation in the V-gene/J-gene junction, resulting in an early stop codon. In contrast, the 3H4 lambda variable region has a properly in-frame V-gene/J-gene junction and aligns to the reference sequence. Therefore, 3H4 lambda is likely the correct 3H4 light chain while 3H4 kappa represents an abortive rearrangement and might originate from a hybridoma fusion partner transcript. An amino acid sequence comparison of 3H4 kappa and 3H4 lambda can be seen in FIG. 3, in which the alignment and coloring were performed with Jalview. (Reference 32) The values given in Tables 3 and 4 are for 3H4 lambda.

Example 4—Verification of Antigen Binding: Comparison of Chimeric mAb 2D9 and Mouse mAb 2D9

To validate the determined antibody sequences, the heavy and light chain regions from each hybridoma were cloned, expressed, and purified. Recombinant antibody constructs comprised of the variable regions from the original mouse antibody and the constant regions from the human IgG1 antibody VRC01. (References 23,24) were generated. These constructs are referred to herein as chimeric monoclonal antibodies. Using antibody 2D9 as a representative sample, chimeric mAb 2D9 was compared to its corresponding mouse antibody. Chimeric mAb 2D9 was transiently expressed in human embryonic kidney (HEK) 293F cells and purified from the medium by Protein A beads. Mouse mAb 2D9, the original antibody, was isolated from mouse ascites fluid and purified by Protein G beads. An SDS-PAGE gel comparison (FIG. 4A) shows that both the original mouse mAb 2D9 and chimeric mAb 2D9 express light and heavy chains (reducing lanes) that form an antibody complex of the correct size, ~145 kD (non-reducing lanes).

Figure 4:
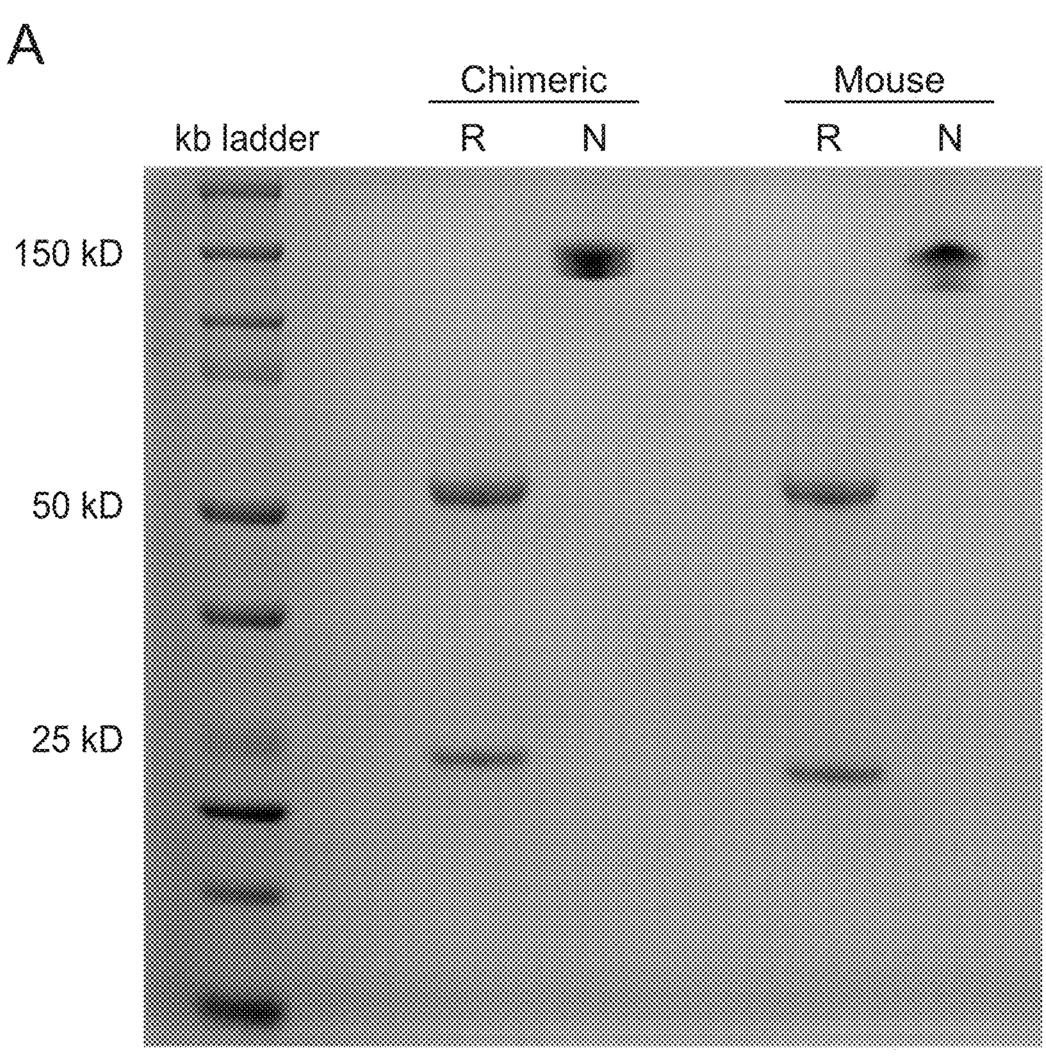
FIG. 4: A comparison of chimeric mAb 2D9 and mouse mAb 2D9. R=reducing gel sample, N=non-reducing gel sample (A) SDS-PAGE gel comparing chimeric mAb 2D9 (left) to mouse mAb 2D9 (right). A reducing (R) and a non-reducing (N) sample is shown for each mAb. (B) Indirect ELISA showing that chimeric mAb 2D9 binds the Spike 8 antigen. (C) Indirect ELISA showing that mouse mAb 2D9 binds the Spike 8 antigen.
Figure 4:
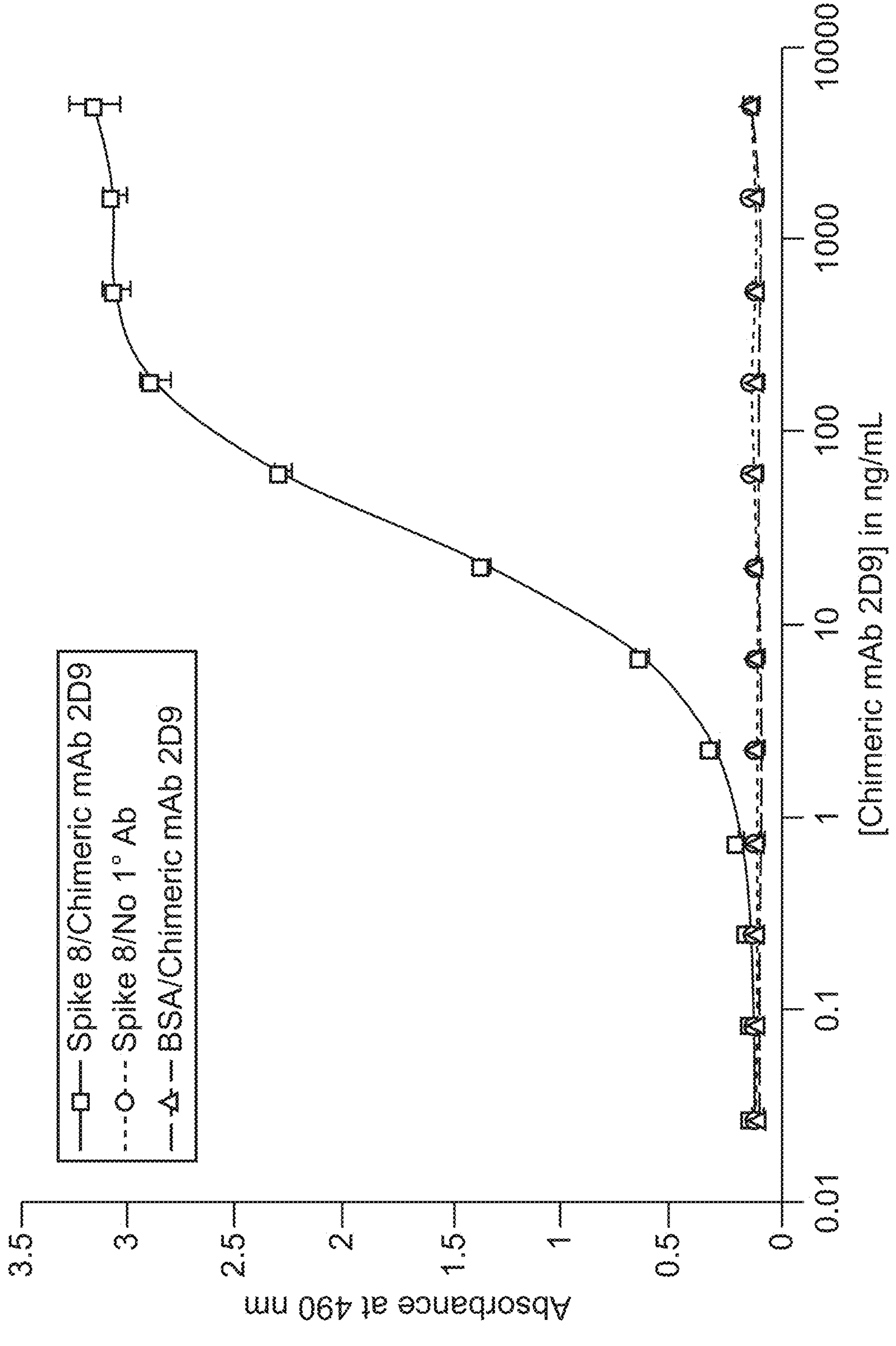
Figure 4:
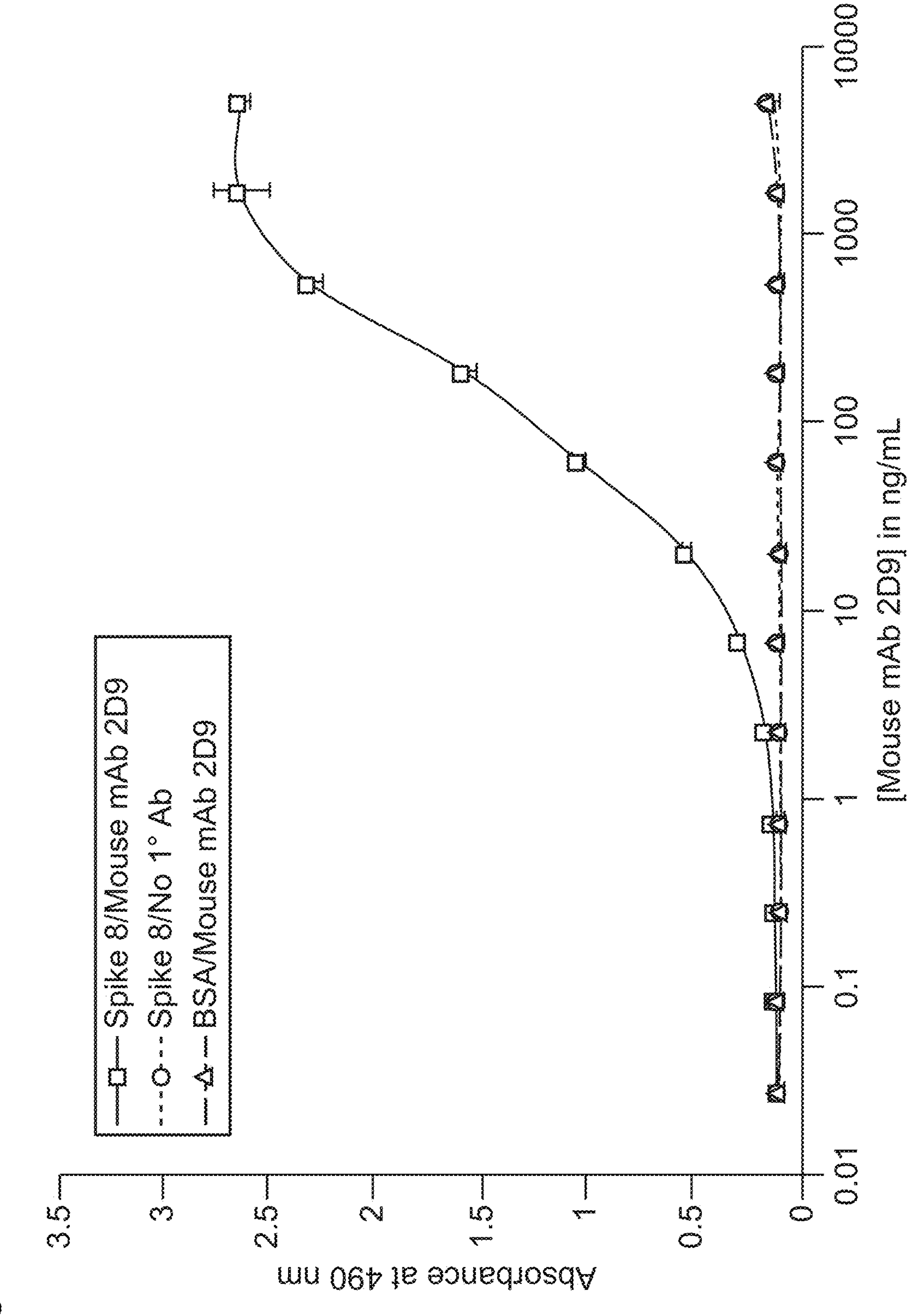

Next, the ability of the recombinant chimeric mAb 2D9 to bind its antigen, Spike 8, the recombinant capsid spike domain from human astrovirus serotype 8, against which mouse mAb 2D9 was raised was tested. (Reference 26). It was shown by indirect ELISA, that both chimeric mAb 2D9 and mouse mAb 2D9 bind Spike 8 (FIGS. 4B and 4C). The other four chimeric mAbs also bind the human astrovirus spike against which they were raised. Thus, the disclosed method of sequencing mouse IgG variable regions resulted in the correct sequences each time since all five recombinant chimeric antibodies constructed with those sequences retained their ability to bind the antigen used to raise the original mouse antibodies. This result indicates a performance rate of 100% for the disclosed method.

Figure 5:
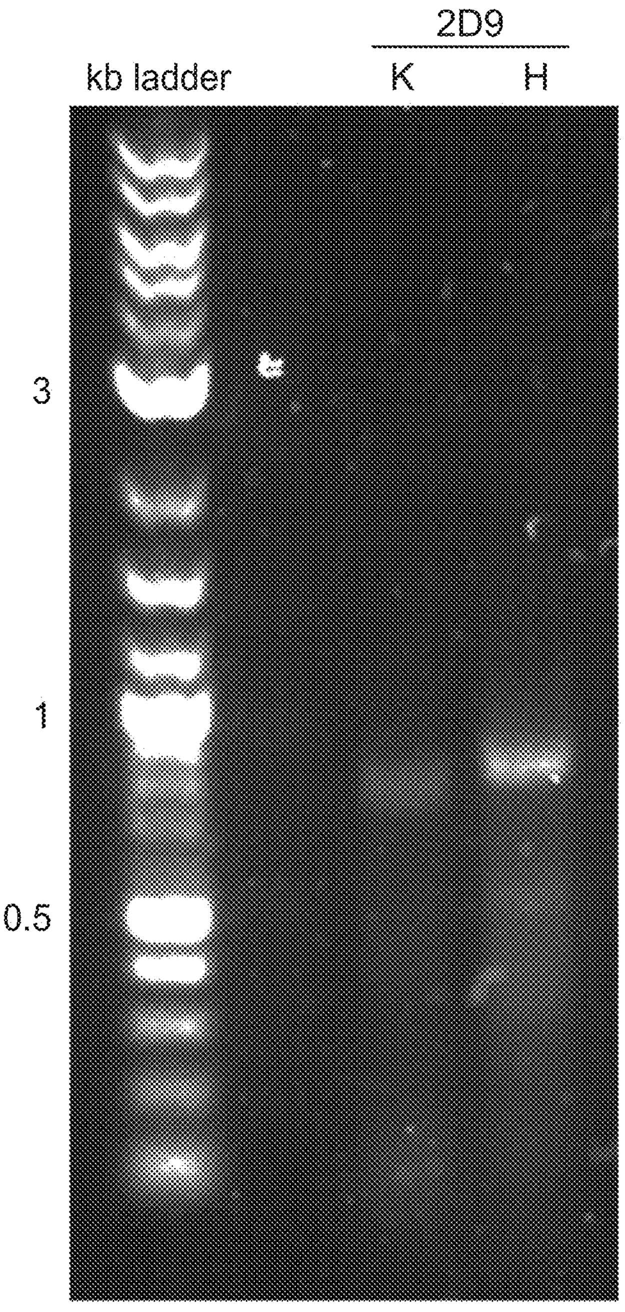
FIG. 5: RT-PCR amplification of chimeric antibody variable regions.

Example 5—RT-PCR Amplification of RNA from Chimeric Antibodies Expressed in a Human Cell Line The success in amplifying and sequencing mouse antibody variable regions from hybridoma RNA led to a proofof-concept experiment where the same RT-PCR method, including cycle conditions, was applied to RNA extracted from HEK 293F cells transiently transfected with chimeric mAb 2D9 plasmid constructs. New RT-PCR reverse primers (Tables 5 and 6) were designed. The new primers were specific for the constant regions of human IgG antibodies rather than mouse IgG antibodies. Since as disclosed above, it was clear that mAb 2D9 contains a kappa chain and a heavy chain and does not have a lambda chain, RT-PCR primers were designed only for human kappa and IgG heavy chains. As shown in FIG. 5, RT-PCR using the human primers on RNA extracted from HEK 293F cells was equally as successful as RT-PCR using the mouse primers on hybridoma RNA (FIG. 2B). Therefore, we conclude that our method can be applied for the sequencing of human IgG variable regions as well as mouse IgG variable regions.

that 45% of plasmid clones sent for sequencing contained DNA encoding antibody variable regions (Table 3). This percentage might be improved by purification of the RT-PCR product by gel extraction before blunt-end cloning rather than purification only by a PCR clean-up kit. Alternatively, Gibson assembly may be used to clone the RT-PCR products into a plasmid containing the template-switch oligonucleotide and reverse primer sequences.

Another advantage of this method is that it is not necessary to know if a monoclonal antibody contains a kappa or a lambda chain before RT-PCR amplification. RT-PCR reactions can be set up for both types of light chain. In the results disclosed herein, for four of five hybridomas utilized a kappa chain, as the lambda chain did not amplify. In the fifth case, Sanger sequencing distinguished between 3H4 kappa and 3H4 lambda and showed that 3H4 lambda chain is full-length. Thus, this method enables distinction between the two types of light chain.

TABLE 5

Human IgG reverse transcription primers.

| Primer Name | Forward or Reverse | Primer Sequence |
|---|---|---|
| Template-switch oligo | Universal forward primer | As above in Table 1 |
| hIGK RT | Reverse primer for kappa chain | 5' gattggagggcgttatccacc 3' (SEQ ID NO: 9) |
| hIGHG RT | Reverse primer for heavy chain | 5' gccgggaaggtgtgcacg 3' (SEQ ID NO: 10) |

TABLE 6

Human IgG PCR primers

| Primer Name | Forward or Reverse | Primer Sequence |
|---|---|---|
| ISPCR | Universal forward primer | As above in Table 2 |
| hIGH PCR | Reverse primer for kappa chain | 5' tttggcctctctgggatagaag 3' (SEQ ID NO: 11) |
| hIGHG PCR | Reverse primer for heavy chain | 5' agggcgcctgagttccacg 3' (SEQ ID NO: 12) |

As for mouse, a Clustal Omega (Reference 29) multiple sequence alignment (not shown) of the constant regions from all subclasses of human IgG (IgG1, IgG2, IgG3, and IgG4) was performed using sequences available on IMGT. (Reference 30). hIGHG RT and hIGHG PCR can potentially prime from the constant regions of human antibodies of all IgG subclasses because of a high degree of sequence conservation in the priming regions, with a maximum of one mismatch between the primers and a particular IgG subclass' constant regions. Because of this high degree of conservation, it can be anticipated that the disclosed primers may be used to sequence antibodies from all human IgG subclasses.

The disclosed methods can potentially be implemented to determine the variable region sequences of any antibody, provided that the proper constant region reverse primers for the antibody of interest are constructed. This feature makes the disclosed approach broadly applicable for many users.

The RT-PCR basis of the method allows for sequence determination of multiple antibody samples at once by simply setting up several RT-PCR reactions in parallel. In addition, a small RNA sample is sufficient; each RT-PCR reaction was set up with only 100 ng of cellular RNA. Note Methods Hybridoma production and total RNA extraction: The hybridoma cells producing monoclonal antibodies were generated as described in Reference 26. Total RNA was extracted from the hybridoma cells using TRIzol Reagent (Invitrogen, 15596026) according to the manufacturer's instructions.

Reverse transcription to synthesize cDNA of antibody variable regions: The SMARTScribe Reverse Transcriptase kit from Clontech (Table 7) was used. Additionally used were RNA samples from hybridomas (five hybridoma RNA samples from the mouse antibodies or one RNA sample from the chimeric antibody), primers (Tables 1 and 2 for mouse antibodies or Tables 5 and 6 for chimeric antibodies), 10 mM deoxynucleotide triphosphate mix (dNTPs), H2O, and an 80 U/μL RNAse inhibitor. Reverse transcription was executed according to the following protocol: All reactions were kept on ice during setup. For each RNA sample, three cDNA synthesis reactions were set up: one for the kappa chain, one for the lambda chain, and one for the heavy chain.

Ideally, only one of the light chains will amplify per antibody. 1. In PCR tubes, Mix #1 was prepared: 2 μL 50 ng/μL RNA, 1 μL 10 μM reverse RT primer based on antibody chain (ex. mIGK RT, mIGL RT, or mIGHG RT for mouse antibodies), and 1 μL 10 mM dNTPs. For one RNA sample, three tubes of Mix #1 were needed, each containing a different reverse primer. 2. In a 0.5 mL Eppendorf tube, Mix #2 was prepared: 1.95 μL H2O, 2 μL 5× SMARTScribe buffer, 1 μL 20 mM DTT, and 0.3 μL 100 μM template-switch oligo. Volumes given for Mix #2 are for one cDNA synthesis reaction, so scale-up occurred as necessary, i.e. three times the volumes for Mix #2 were prepared per hybridoma RNA sample. One master mix of Mix #2 was prepared for all reactions. 3. Any RNA secondary structure was denatured by incubating the tubes containing Mix #1 at 72° C. for 3 minutes in a thermocycler. 4. During denaturation of Mix #1, the following was added to Mix #2: 0.25 μL 80 U/μL RNAse inhibitor and 0.5 μL 100 U/μL SMARTScribe Reverse Transcriptase per cDNA synthesis reaction. 5. 6 μL of Mix #2 was added to each tube of denatured Mix #1. 6. In the thermocycler, the combined mix was incubated at 42° C. for 60 minutes, then at 70° C. for 5 minutes to stop the reaction. The reactions were held at 4° C. PCR amplification was done immediately after reverse transcription. No cDNA purification step was necessary.

TABLE 7

Kits and antibodies

| Purpose | Manufacturer: Catalog Number | Kit Contents or Antibody Details |
|---|---|---|
| Reverse Transcription | Clontech: 639537 | 5x SMARTScribe buffer<br>20 mM DTT<br>100 U/μL SMARTScribe Reverse Transcriptase |
| PCR Clean-Up and Gel Extraction | Macherey-Nagel: 740609.50 | Buffers NTI, NT3, and NE<br>DNA-binding columns |
| Blunt-End Cloning | Invitrogen: 450245 | pCR ™-Blunt II-TOPO ® plasmid<br>Salt solution (1.2M NaCl, 0.06M $MgCl_2$) dNTP mix<br>M13 forward and reverse sequencing primers |
| Miniprep | Macherey-Nagel: 740588.50 | Buffers A1, A2, A3, AW, A4, and AE<br>RNAse A DNA-binding columns |
| Effectene Transfection | Qiagen: 301425 | Effectene<br>Enhancer<br>Buffer EC |
| Pierce Protein A Fab Preparation Kit | Thermo Fisher Scientific: 44985 | Protein A beads IgG elution buffer (pH 2.8, amine-based) |
| Goat Anti-Human IgG Fc Antibody, Horseradish Peroxidase Conjugate, Affinity Purified | Thermo Fisher Scientific: A18817 | Horseradish-peroxidase-conjugated polyclonal 2° antibody with specificity for human antibody Fc region Antibody Registry ID: AB_2535594 |
| Peroxidase-Conjugated AffiniPure Goat Anti-Mouse IgG, Fcγ Fragment Specific | Jackson ImmunoResearch: 115-035-071 | Horseradish-peroxidase-conjugated polyclonal 2° antibody with specificity for mouse antibody Fc region Antibody Registry ID: AB_2338506 |

PCR amplification of antibody variable regions: 1. PCR reactions for each cDNA synthesis were set up: 10 μL 5×PCR buffer, 1 μL 10 mM dNTPs, 3 μL synthesized cDNA from RT reaction, 2.5 μL 10 μM universal forward primer ISPCR, 2.5 μL 10 μM reverse PCR primer based on antibody chain (ex. mIGK PCR, mIGL PCR, or mIGHG PCR for mouse antibodies), 30.5 μL H2O, and 0.5 μL 2 U/μL Phusion polymerase (or other high-fidelity polymerase). 2. A touch-down/step-down PCR was performed according to the following thermocycler conditions: 98° C. for 30 seconds; 10 cycles of 98° C. for 15 seconds, 63-57.5° C. for 30 seconds, and 72° C. for 30 seconds; 15 cycles of 98° C. for 15 seconds, 56° C. for 30 seconds, and 72° C. for 30 seconds; followed by 72° C. for 7 minutes; and holding at 4° C. 3. 5 μL of each RT-PCR reaction was run on a 1% agarose gel in TAE buffer at 90 V. The amplified mouse antibody products appeared between 550-600 base pairs. The amplified human antibody products appeared between 750-850 base pairs. The Quick Load Purple 2-Log DNA Ladder (NEB, N0550S) was used as the standard.

Gel extraction and sequencing or PCR clean-up, blunt-end cloning, miniprep, and sequencing of antibody variable regions: The total volume of each RT-PCR reaction was run on a 1% agarose gel in TAE buffer at 90 V. Bands of interest were excised, and DNA was extracted from the gel using Macherey-Nagel's PCR Clean-Up and Gel Extraction kit (Table 7). The extracted DNA was Sanger sequenced by Sequetech Corporation using the ISPCR primer (Table 2). Alternatively, the RT-PCR reactions were PCR-cleaned using Macherey-Nagel's PCR Clean-Up and Gel Extraction kit (Table 7). 2 μL of each PCR-cleaned product was blunt-end cloned into the pCR-Blunt-II-TOPO vector according to the blunt-end cloning kit manual (Table 7). Next, 3 μL of each TOPO cloning reaction was transformed into chemically competent *E. coli.* 100 μL of each transformation was spread on LB plates containing 50 μg/mL kanamycin and incubated at 37° C. overnight. After obtaining colonies, 5-10 colonies per antibody chain were inoculated in 5 mL LB/kanamycin medium and grown at 37° C. with 250 rpm shaking overnight. These cultures were miniprepped using Macherey-Nagel's miniprep kit (Table 7) and the resulting plasmid DNA was Sanger sequenced by Sequetech Corporation using the M13 forward primer.

A custom-written Python program was used to identify amplicons and plasmid clones containing antibody variable region sequences. The sequences originating from the same *E. coli* transformation, corresponding to a specific chain from a specific antibody, were then aligned using Clustal Omega to check for sequence consensus of the antibody chain. The final DNA sequence for each antibody variable region was submitted to IgBLAST with default parameters and mouse selected as the organism for query sequence to determine percent identity to the IgBLAST reference sequences for light and for heavy chains.

Expression and purification of the Spike 8 antigen: A synthetic gene codon-optimized for *E. coli* expression encoding the human astrovirus serotype 8 capsid spike protein amino acids 424 to 648 (Spike 8, UniProtKB entry Q91FX1) was purchased. To make the Spike 8 expression plasmid, the gene was cloned into pET52b (Addgene) in-frame with a C-terminal thrombin cleavage site and a 10-histidine purification tag. The plasmid was verified by DNA sequencing. Next, the plasmid was transformed into *E. coli* strain BL21 (DE3). Cultures were inoculated and grown in LB/ampicillin medium. At an optical density of 0.6, protein production was induced with 1 mM isopropyl-D-thiogalactopyranoside (IPTG) at 18° C. for 18 hours. *E. coli* cells were lysed by ultrasonication in 20 mM Tris-HCl pH 8.0, 500 mM NaCl, and 20 mM imidazole (Buffer A) containing 2 mM MgCl2, 0.0125 U/μL benzonase (Merck Millipore, 71205), and 1× protease inhibitor cocktail set V EDTA-Free (Merck Millipore, 539137). Proteins were batch purified from soluble lysates with TALON metal affinity resin (GE Healthcare, 28-9574-99) and eluted with Buffer A containing 500 mM imidazole. Proteins were dialyzed overnight into 10 mM Tris-HCl pH 8.0, 150 mM NaCl (TBS) and further purified in TBS by size exclusion chromatography on a Superdex 75 column.

Expression and purification of chimeric mAb 2D9: A synthetic gene codon-optimized for insect cell expression containing the 2D9 kappa and heavy chain variable regions connected by a linker was ordered. The kappa and heavy chain variable regions were amplified separately and individually cloned by Gibson assembly into the two pCMV-VRC01 antibody backbone vectors for light and for heavy chains, which contain the constant regions of VRC01, a human anti-HIV antibody targeting the gp120 protein. (References 23-25). The resulting expression plasmids, pCMV-VRC01_2D9_kappa and pCMV-VRC01_2D9_heavy, contain the variable regions from the original mouse antibody 2D9 and the constant regions from a human IgG1 antibody under control of the human cytomegalovirus promoter. This same cloning procedure was accomplished with the four remaining antibodies. All plasmids were verified by DNA sequencing. Using the Effectene Transfection kit (Table 7), 2 μg of each of the 2D9 constructs was transiently co-transfected into HEK 293F cells (Thermo Scientific, R79007) obtained from a neighboring laboratory. The HEK 293F cells were seeded the day before at $0.5\times10^6$ cells/mL in 10 mL FreeStyle 293 medium (Gibco, 12338018). After 8 days of incubation at 37° C. with 5% CO2, chimeric mAb 2D9 was purified from the HEK 293F cell medium with Protein A beads (Table 7). Chimeric mAb 2D9 was eluted with IgG elution buffer (pH 2.8, amine-based), and the elution was immediately neutralized with 2.0 M Tris pH 8.0.

Total RNA extraction from transfected HEK 293F cells: The extraction of RNA from HEK 293F cells transiently transfected with expression plasmids for chimeric mAb 2D9 was done according to the manufacturer's protocol for using TRIzol Reagent (Invitrogen, 15596026) to extract total RNA from cells grown in a monolayer. 3 mL TRIzol Reagent was used per T75 flask seeded 8 days prior with 10 mL of $0.5\times10^6$ HEK 293F cells/mL.

Purification of mouse mAb 2D9: Mouse mAb 2D9 was purified from mouse ascites fluid with Protein G beads (Thermo Scientific, 20398). Mouse mAb 2D9 was eluted with IgG elution buffer (pH 2.8, amine-based), and the elution was immediately neutralized with 2.0 M Tris pH 8.0.

SDS-PAGE gel comparing chimeric mAb 2D9 and mouse mAb 2D9: Each SDS-PAGE gel sample was prepared with 4 μg protein. For each monoclonal antibody, a reducing sample and a non-reducing sample was prepared. For the reducing samples, purified protein was mixed with 5×SDS loading dye and boiled at 100° C. for 7 minutes. For the non-reducing samples, purified protein was mixed with 5× loading dye not containing SDS and not boiled. The protein samples were loaded on a pre-cast 4-12% Bis-Tris gel (Novex Life Technologies, NP0321 BOX) and run in MES-SDS buffer at 140 V. The gel was stained by Coomassie Blue. The Precision Plus Protein Dual Color Standard (Bio-Rad, 1610374) was used as the standard.

ELISAs comparing Spike 8 binding by chimeric mAb 2D9 and mouse mAb 2D9: Each point was performed in triplicate. 150 μL per well of Spike 8 at 5 μg/mL in phosphate-buffered saline (PBS) was incubated overnight at room temperature on two 96-well ELISA microtiter plates. As a control, 150 μL per well of 5 μg/mL bovine serum albumin (BSA) in PBS was also incubated overnight. The plates were then washed three times with PBS containing 0.05% Tween 20 (PBST). The wells were blocked by adding 150 μL of 5% BSA in PBS to each well and incubating at room temperature for 1 hour followed by three PBST washes. Chimeric mAb 2D9 and mouse mAb 2D9, the primary antibodies, were diluted to 5 μg/ml with 1% BSA in PBS. 150 μL of chimeric mAb 2D9 was added to wells in the first column of one ELISA plate and serially diluted 1:3 with 1% BSA in PBS. This serial dilution was repeated on the other ELISA plate with mouse mAb 2D9. As a control, three rows of 5 μg/mL Spike 8 on each plate were left without primary antibody; 150 μL of 1% BSA in PBS was added instead to the first wells of these rows and serially diluted 1:3. The plates were incubated for 1 hour at room temperature and then washed three times with PBST.

For the ELISA in which the primary antibody was chimeric mAb 2D9, the plate was incubated for 1 hour at room temperature with 150 μL per well of secondary antibody, a goat anti-human IgG Fc antibody conjugated to horseradish peroxidase (HRP) (Table 7) diluted 1:20,000 with 1% BSA in PBS. For the ELISA in which the primary antibody was mouse mAb 2D9, the plate was incubated for 1 hour at room temperature with 150 μL per well of secondary antibody, a goat anti-mouse IgG Fc antibody conjugated to HRP (Table 7) diluted 1:8,500 with 1% BSA in PBS. Then the plates were washed three times with PBST and developed by adding 150 μL of 0.4 mg/mL horseradish peroxidase substrate o-phenylenediamine dihydrochloride (OPD) (Thermo Scientific, 34006) in 0.05 M phosphate-citrate buffer (pH 5.0) with 0.015% hydrogen peroxide for 10 minutes at room temperature. The reactions were stopped by incubation with 150 μL of 2 N sulfuric acid for 10 minutes at room temperature. The absorbance was measured at 490 nm.

Software availability: The custom Python program written to analyze Sanger sequencing data is available at: github.com/Lena-Meyer/findAntibodies

| Abbreviation | Meaning |
|---|---|
| BSA | Bovine serum albumin |
| CDR | Complementarity-determining region |
| ELISA | Enzyme-linked immunosorbent assay |
| HEK 293F | Human embryonic kidney cell line |
| IgG1 | Immunoglobulin G subclass 1 |
| mAb | Monoclonal antibody |
| MMLV | Moloney murine leukemia virus |
| RACE | Rapid amplification of 5' cDNA ends |
| RT-PCR | Reverse transcription |
| PCR | polymerase chain reaction |
| SMART | Switching mechanism at 5' end of RNA transcript |
| Spike 8 | Recombinant capsid spike domain from human astrovirus serotype 8 |

REFERENCES

1 Frenzel, A., Hust, M. & Schirrmann, T. Expression of recombinant antibodies. *Front Immunol* 4, 217, doi: 10.3389/fimmu.2013.00217 (2013).

2 Coco-Martin, J. M., Oberink, J. W., van der Velden-de Groot, T. A. M. & Beuvery, E. C. Methods for studying the stability of antibody expression by hybridoma cells in homogeneous continuous culture systems. Analytica Chimica Acta 249, 257-262, 542 doi:doi.org/10.1016/0003-2670 (91) 87031-2 (1991).

3 Kuniyoshi, Y. et al. Identification of Immunoglobulin Gene Sequences from a Small Read Number of mRNA-Seq Using Hybridomas. *PLoS One* 11, e0165473, 545 doi:10.1371/journal.pone.0165473 (2016).

4 Schanz, M. et al. High-throughput sequencing of human immunoglobulin variable regions with subtype identification. *PLoS One* 9, e111726, doi:10.1371/journal-.pone.0111726 548 (2014).

5 Henry, K. A. Next-Generation DNA Sequencing of VH/VL Repertoires: A Primer and Guide to Applications in Single-Domain Antibody Discovery. *Methods Mol Biol* 1701, 425-446, 551 doi:10.1007/978-1-4939-7447-4_24 (2018).

6 Wang, Z. et al. Universal PCR amplification of mouse immunoglobulin gene variable regions: the design of degenerate primers and an assessment of the effect of DNA polymerase 3' to 5' exonuclease activity. *J Immunol Methods* 233, 167-177 (2000).

7 Krebber, A. et al. Reliable cloning of functional antibody variable domains from hybridomas and spleen cell repertoires employing a reengineered phage display system. *J Immunol Methods* 201, 35-55 (1997).

8 Ihle, Ø., Beckstrom, K. J. & Michaelsen, T. E. Cloning, sequencing and expression of immunoglobulin variable regions of murine monoclonal antibodies specific for the P1.7 and P1.16 PorA protein loops of *Neisseria meningitidis. Scand J Immunol* 57, 453-462 561 (2003).

9 Koren, S., Kosmač, M., Colja Venturini, A., Montanič, S. & Čurin Šerbec, V. Antibody variable-region sequencing as a method for hybridoma cell-line authentication. *Appl Microbiol Biotechnol* 78, 1071-1078, doi:10.1007/s00253-008-1386-5 (2008)

10 Ruberti, F., Cattaneo, A. & Bradbury, A. The use of the RACE method to clone hybridoma cDNA when V region primers fail. *J Immunol Methods* 173, 33-39 (1994).

11 Doenecke, A., Winnacker, E. L. & Hallek, M. Rapid amplification of cDNA ends (RACE) improves the PCR-based isolation of immunoglobulin variable region genes from murine and human lymphoma cells and cell lines. *Leukemia* 11, 1787-1792 (1997).

12 Kosmač, M., Koren, S., Škrlj, N., Dolinar, M. & Čurin Šerbec, V. in *DNA Fingerprinting Sequencing and Chips DNA properties and modifications, functions and interactions, recombination and applications series* (eds K. Ovesen & U. Matthiesen) Ch. 3, (Nova Biomedical Books, 2009).

13 Babrak, L., McGarvey, J. A., Stanker, L. H. & Hnasko, R. Identification and verification of hybridoma-derived monoclonal antibody variable region sequences using recombinant DNA technology and mass spectrometry. *Mol Immunol* 90, 287-294, doi:10.1016/j.molimm.2017.08.014 (2017).

14 Bandeira, N., Pham, V., Pevzner, P., Arnott, D. & Lill, J. R. Automated de novo protein sequencing of monoclonal antibodies. *Nat Biotechnol* 26, 1336-1338, doi:10.1038/nbt1208-1336 (2008).

15 Castellana, N. E. et al. Resurrection of a clinical antibody: template proteogenomic de novo proteomic sequencing and reverse engineering of an anti-lymphotoxin-alpha antibody. *Proteomics* 11, 395-405, doi:10.1002/pmic.201000487 (2011).

16 Sen, K. I. et al. Automated Antibody De Novo Sequencing and Its Utility in Biopharmaceutical Discovery. *J Am Soc Mass Spectrom* 28, 803-810, doi:10.1007/s13361-016-1580-0 (2017).

17 Rickert, K. W. et al. Combining phage display with de novo protein sequencing for reverse engineering of monoclonal antibodies. *MAbs* 8, 501-512, doi:10.1080/19420862.2016.1145865 (2016).

18 Bogdanoff, W. A. et al. De Novo Sequencing and Resurrection of a Human Astrovirus-Neutralizing Antibody. *ACS Infect Dis* 2, 313-321, doi:10.1021/acsinfecdis.6b00026 (2016).

19. Genscript Antibody Sequencing Services, www.genscript.com

20. SydLabs Antibody Sequencing Services, www.sydlabs.com

21. FusionAntibodies Antibody Sequencing Services, www.fusionantibodies.com

22. LakePharma Antibody Variable Region Sequencing and Cloning, www.lakepharma.com 23 Zhou, T. et al. Structural basis for broad and potent neutralization of HIV-1 by antibody VRC01. *Science* 329, 811-817, doi:10.1126/science.1192819 (2010).

24 Wu, X. et al. Maturation and Diversity of the VRC01-Antibody Lineage over 15 Years of Chronic HIV-1 Infection. *Cell* 161, 470-485, doi:10.1016/j.cell.2015.03.004 (2015).

25 Barouch, D. H. et al. A human T-cell leukemia virus type 1 regulatory element enhances the immunogenicity of human immunodeficiency virus type 1 DNA vaccines in mice and nonhuman primates. *J Virol* 79, 8828-8834, doi:10.1128/JVI.79.14.8828-8834.2005 (2005).

26. Espinosa, R. et al. Isolation of neutralizing monoclonal antibodies to human astrovirus and characterization of virus variants that escape neutralization. J Virol, doi:10.1128/JVI.01465-18 (2018).

27 Takara. SMART Technology Overview, takarabio.com/learning-centers/next-generation-sequencing/technology-and-application-overviews/smart-technology 28 Zhu, Y. Y., Machleder, E. M., Chenchik, A., Li, R. & Siebert, P. D. Reverse transcriptase template switching: a SMART approach for full-length cDNA library construction. *Biotechniques* 30, 892-897, doi:10.2144/01304pf02 (2001).

29 Sievers, F. et al. Fast, scalable generation of high-quality protein multiple sequence alignments using Clustal Omega. *Mol Syst Biol* 7, 539, doi:10.1038/msb.2011.75 (2011).

30 Lefranc, M. P. IMGT, The International ImMunoGeneTics Information System, imgt.cines.fr. *Methods Mol Biol* 248, 27-49 (2004).

31 Ye, J., Ma, N., Madden, T. L. & Ostell, J. M. IgBLAST: an immunoglobulin variable domain sequence analysis tool. *Nucleic Acids Res* 41, W34-40, doi:10.1093/nar/gkt382 (2013).

32 Waterhouse, A. M., Procter, J. B., Martin, D. M., Clamp, M. & Barton, G. J. Jalview Version 2—a multiple sequence alignment editor and analysis workbench. *Bioinformatics* 25, 1189-1191, doi:10.1093/bioinformatics/btp033 (2009).

What is claimed is:

1. A method of sequencing the variable regions of a human monoclonal antibody produced by a hybridoma cell line, wherein the human monoclonal antibody comprises a heavy chain and a kappa light chain, the method comprising:

(a) annealing in a first reaction tube a heavy chain constant region-specific reverse transcription primer to the constant region of heavy chain transcripts extracted from cells of the hybridoma cell line, wherein the heavy chain transcripts encode the heavy chain constant and variable regions of the human monoclonal antibody;

(b) extending the heavy chain constant region-specific reverse transcription primer using a reverse transcriptase to synthesize a heavy chain complementary DNA (cDNA), wherein the heavy chain cDNA comprises a 3' overhang produced by the reverse transcriptase;

(c) annealing a template switch oligonucleotide comprising a primer sequence to the 3' overhang and extending the 3' end of the heavy chain cDNA using the template switch oligonucleotide as template;

(d) performing second strand synthesis on the heavy chain cDNA using a primer comprising the primer sequence of the template switch oligonucleotide annealed at step (c) to produce a double-stranded heavy chain cDNA;

(e) PCR amplifying the double-stranded heavy chain cDNA using a primer comprising the primer sequence of the template switch oligonucleotide annealed at step (c) and a human heavy chain constant region-specific primer that anneals to a sequence nested within the cDNA sequence synthesized during step (b) to produce heavy chain cDNA amplicons, wherein the human heavy chain constant region-specific primer that anneals to a sequence nested within the cDNA sequence synthesized during step (b) consists of the nucleotide sequence agggcgcctgagttccacg (SEQ ID NO: 12);

(f) annealing in a second reaction tube a human light chain constant region-specific reverse transcription primer to the constant region of human light chain transcripts extracted from cells of the hybridoma cell line, wherein the light chain transcripts encode the human light chain constant and variable regions of the human monoclonal antibody;

(g) extending the human light chain constant region-specific reverse transcription primer using a reverse transcriptase to synthesize a light chain cDNA, wherein the light chain cDNA comprises a 3' overhang produced by the reverse transcriptase;

(h) annealing a template switch oligonucleotide comprising a primer sequence to the 3' overhang and extending the 3' end of the light chain cDNA using the template switch oligonucleotide as template;

(i) performing second strand synthesis on the light chain cDNA using a primer comprising the primer sequence of the template switch oligonucleotide annealed at step (h) to produce a double-stranded light chain cDNA;

(j) PCR amplifying the double-stranded light chain cDNA using a primer comprising the primer sequence of the template switch oligonucleotide annealed at step (h) and a human light chain constant region-specific primer that anneals to a sequence nested within the cDNA sequence synthesized during step (g) to produce light chain cDNA amplicons, wherein the human light chain constant region-specific primer that anneals to a sequence nested within the cDNA sequence synthesized during step (g) consists of the nucleotide sequence tttggcctctctgggatagaag (SEQ ID NO: 11); and (k) performing Sanger sequencing on the heavy chain cDNA amplicons and the kappa chain cDNA amplicons, thereby sequencing the variable regions of the human monoclonal antibody produced by the hybridoma cell line.

2. The method according to claim 1, wherein the heavy chain constant region-specific reverse transcription primer comprises the nucleotide sequence gccgggaaggtgtgcacg (SEQ ID NO: 10) or a nucleotide sequence having at least 90% sequence identity to SEQ ID NO: 10, and the kappa chain constant region-specific reverse transcription primer comprises the nucleotide sequence gattggagggcgttatccacc (SEQ ID NO: 9) or a nucleotide sequence having at least 90% sequence identity to SEQ ID NO: 9.

3. The method according to claim 1, wherein the reverse transcriptase is an MMLV reverse transcriptase.

4. The method according to claim 1, wherein the heavy chain cDNA amplicons and the kappa chain cDNA amplicons are cloned into a vector prior to step (k).

* * * * *

SEQUENCE LISTING

```
<160> NUMBER OF SEQ ID NOS: 14

<210> SEQ ID NO 1
<211> LENGTH: 30
```

```
<212> TYPE: DNA
<213> ORGANISM: Mus musculus
<220> FEATURE:
<221> NAME/KEY: misc_feature
<222> LOCATION: (28)..(30)
<223> OTHER INFORMATION: The nucleic acids from position 28 to position
      30 are riboguanine.

<400> SEQUENCE: 1

aagcagtggt atcaacgcag agtacatggg                                   30


<210> SEQ ID NO 2
<211> LENGTH: 22
<212> TYPE: DNA
<213> ORGANISM: Mus musculus

<400> SEQUENCE: 2

ttgtcgttca ctgccatcaa tc                                           22


<210> SEQ ID NO 3
<211> LENGTH: 21
<212> TYPE: DNA
<213> ORGANISM: Mus musculus

<400> SEQUENCE: 3

ggggtaccat ctaccttcca g                                            21


<210> SEQ ID NO 4
<211> LENGTH: 20
<212> TYPE: DNA
<213> ORGANISM: Mus musculus

<400> SEQUENCE: 4

agctgggaag gtgtgcacac                                              20


<210> SEQ ID NO 5
<211> LENGTH: 22
<212> TYPE: DNA
<213> ORGANISM: Mus musculus

<400> SEQUENCE: 5

aagcagtggt atcaacgcag ag                                           22


<210> SEQ ID NO 6
<211> LENGTH: 24
<212> TYPE: DNA
<213> ORGANISM: Mus musculus

<400> SEQUENCE: 6

acattgatgt ctttggggta gaag                                         24


<210> SEQ ID NO 7
<211> LENGTH: 20
<212> TYPE: DNA
<213> ORGANISM: Mus musculus

<400> SEQUENCE: 7

atcgtacaca ccagtgtggc                                              20


<210> SEQ ID NO 8
<211> LENGTH: 20
<212> TYPE: DNA
<213> ORGANISM: Mus musculus

<400> SEQUENCE: 8
```

gggatccaga gttccaggtc 20

<210> SEQ ID NO 9
<211> LENGTH: 21
<212> TYPE: DNA
<213> ORGANISM: Mus musculus

<400> SEQUENCE: 9
gattggaggg cgttatccac c 21

<210> SEQ ID NO 10
<211> LENGTH: 18
<212> TYPE: DNA
<213> ORGANISM: Mus musculus

<400> SEQUENCE: 10
gccgggaagg tgtgcacg 18

<210> SEQ ID NO 11
<211> LENGTH: 22
<212> TYPE: DNA
<213> ORGANISM: Mus musculus

<400> SEQUENCE: 11
tttggcctct ctgggataga ag 22

<210> SEQ ID NO 12
<211> LENGTH: 19
<212> TYPE: DNA
<213> ORGANISM: Mus musculus

<400> SEQUENCE: 12
agggcgcctg agttccacg 19

<210> SEQ ID NO 13
<211> LENGTH: 108
<212> TYPE: PRT
<213> ORGANISM: Mus musculus

<400> SEQUENCE: 13

```
Asp Ile Val Leu Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp Lys
            100                 105
```

<210> SEQ ID NO 14
<211> LENGTH: 109
<212> TYPE: PRT
<213> ORGANISM: Mus musculus

<400> SEQUENCE: 14

-continued

```
Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Ser Trp Val Gln Glu Lys Pro Asp His Leu Phe Ile Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Asp Asp Glu Ala Ile Tyr Phe Cys Ala Leu Trp Phe Ser Asn
                85                  90                  95

His Trp Val Phe Gly Gly Gly Thr Lys Leu Thr Val Leu
            100                 105
```